United States Patent [19]

Bhatnagar et al.

[11] Patent Number: 5,830,867
[45] Date of Patent: Nov. 3, 1998

[54] HEMOREGULATORY PEPTIDES FOR STIMULATING THE MYELOPOIETIC SYSTEM

[75] Inventors: Pradip Kumar Bhatnagar, Exton; Dirk Heerding, Ardmore, both of Pa.; Peter Martin Fischer, Oslo, Norway

[73] Assignees: SmithKline Beecham Corporation, Philadelphia, Pa.; Nycomed Pharma AS, Oslo, Norway

[21] Appl. No.: 553,562
[22] PCT Filed: May 24, 1994
[86] PCT No.: PCT/US94/05859
  § 371 Date: Jan. 30, 1996
  § 102(e) Date: Jan. 30, 1996
[87] PCT Pub. No.: WO94/27627
  PCT Pub. Date: Dec. 8, 1994

Related U.S. Application Data

[63] Continuation-in-part of Ser. No. 66,952, May 24, 1993, abandoned, and Ser. No. 150,524, Nov. 9, 1993, abandoned.
[51] Int. Cl.⁶ .................. A61K 31/44; A61K 31/505; C07D 403/04; C07D 401/04
[52] U.S. Cl. .............. 514/18; 514/19; 530/332; 530/323
[58] Field of Search ............... 514/18, 19; 530/323, 530/332

[56] References Cited

U.S. PATENT DOCUMENTS

| | | | |
|---|---|---|---|
| 4,310,517 | 1/1982 | Etschenberg et al. | 424/177 |
| 4,732,970 | 3/1988 | Fields et al. | 530/323 |
| 4,859,654 | 8/1989 | Hoover et al. | 514/19 |

FOREIGN PATENT DOCUMENTS

A-0307662  3/1989  European Pat. Off. .

OTHER PUBLICATIONS

R.P. Soni, "Studies in Heterocyclics: Novel Synthsis of 4,5–Diarylimidazoles", *Aust. J. Chem.*, 35, pp. 1493–1496 (1982).

*Primary Examiner*—Matthew V. Grumbling
*Attorney, Agent, or Firm*—Linda E. Hall; Stephen A. Venetianer; Edward T. Lentz

[57] ABSTRACT

The invention provides compounds of the general formula (I):

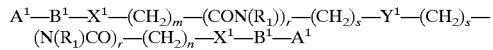

The compounds of this invention are also illustrated by the Formula (II):

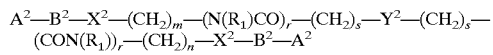

The compounds have hemoregulatory activities and can be used to stimulate haematopoiesis and for the prevention and treatment of viral, fungal and bacterial infectious diseases.

13 Claims, No Drawings

HEMOREGULATORY PEPTIDES FOR STIMULATING THE MYELOPOIETIC SYSTEM

This application claims priority from PCT/US94/05859, filed May 24, 1994 which is a CIP of 08/066,952, filed May 24, 1993, and 08/150,524, Nov. 9, 1993, both abandoned.

FIELD OF THE INVENTION

The present invention relates to novel compounds which have hemoregulatory activities and can be used to stimulate haematopoiesis and for the treatment of viral, fungal and bacterial infectious diseases.

BACKGROUND OF THE INVENTION

A variety of regulatory messengers and modifiers such as colony stimulating factors, interferons, and different types of peptides are responsible for the regulation of myelopoiesis. Metcalf, *Cell*, 43:5 (1985); Baserga R., Foa P., Metcalf D, Polli EE (eds), *Biological Regulation of Cell Proliferation* (1986); Nicola et al., *J. Cell Physiol.* 128:501 (1986), Zoumbos et al., *Proyr. Hemat.* 1:341 and 14:201 (1986); Werner et al., *Experientia* 42:521 (1986).

In 1982, a synthetic hemoregulatory pentapeptide was reported to have a selective inhibitory effect on myelopoietic cells both in vitro and in vivo, where the main effect seems to be on myelopoietic stem cells (CFU-gm), Paukovits et al., Z. Naturforsch 37:1297 (1982) and U.S. Pat. No. 4,499,081. This peptide is believed to be an analogue of a naturally occurring granulopoiesis inhibition factor which has been found in minute quantities in bone marrow extracts.

In 1987, Laerum et al., reported that the oxidation product of this peptide was a dimer (HP-5) formed by disulfide bridges. This dimer has the opposite effects of the monomer as it strongly stimulates colony formation of both human and murine CFU-gm in vitro and up-regulates murine myelopoietic cells in vivo. It is claimed in European Application No. 87309806.5.

The dimer is reported as being useful in stimulating myelopoiesis in patients suffering from reduced myelopoietic activity, including bone marrow damage, agranulocytosis and aplastic anemia including patients having depressed bone marrow function due to immunosuppressive treatment to suppress tissue reactions i.e. in bone marrow transplant surgery. It may also be used to promote more rapid regeneration of bone marrow after cytostatic chemotherapy and radiation therapy for neoplastic and viral diseases. It may be of particular value where patients have serious infections due to a lack of immune response following bone marrow failure.

We have now found certain novel compounds which have a stimulative effect on myelopoietic cells and are useful in the treatment and prevention of viral, fungal and bacterial diseases.

SUMMARY OF THE INVENTION

This invention comprises compounds, hereinafter represented as Formula (I), which have hemoregulatory activities and can be used to stimulate haematopoiesis and in the prevention and treatment of bacterial, viral and fungal diseases.

These compounds are useful in the restoration of leukocytes in patients with lowered cell counts resulting from a variety of clinical situations, such as surgical induced myelosuppression, AIDS, ARDS, congenital myelodysplacis, bone marrow and organ transplants; in the protection of patients with leukopenia from infection; in the treatment of severely burned patients and in the amelioration of the myelosuppression observed with some cell-cycle specific antiviral agents and in the treatment of infections in patients who have had bone marrow transplants, especially those with graft versus host disease, in the treatment of tuberculosis and in the treatment of fevers of unknown origin in humans and animals. The compounds are also useful in the treatment and prevention of viral, fungal and bacterial infectious diseases, particularly Candida, Herpes and hepatitis in both immunosuppressed and "normal" subjects.

These compounds may also be used in combination with the monomers of co-pending U.S. application Ser. No. 07/799,465 and U.S. Pat. No. 4,499,081, incorporated by reference herein, to provide alternating peaks of high and low activity in the bone marrow cells, thus augmenting the natural circadian rhythm of haematopoiesis. In this way, cytostatic therapy can be given at periods of low bone marrow activity, thus reducing the risk of bone marrow damage, while regeneration will be promoted by the succeeding peak of activity. This invention is also a pharmaceutical composition, which comprises a compound of Formula (I) and a pharmaceutically acceptable carrier.

This invention further constitutes a method for stimulating the myelopoietic system of an animal, including humans, which comprises administering to an animal in need thereof, an effective amount of a compound of Formula (I).

This invention also constitutes a method for preventing and treating viral, fungal and bacterial infections in immunosuppressed and normal animals, including humans, which comprises administering to an animal in need thereof, an effective amount of a compound of Formula (I).

DETAILED DESCRIPTION OF THE INVENTION

The compounds of this invention are illustrated by the Formula (I):

$$A^1-B^1-X^1-(CH_2)_m-(CON(R_1))_r-(CH_2)_s-Y^1-(CH_2)_s-(N(R_1)CO)_r-(CH_2)_n-X^1-B^1-A^1 \quad (I)$$

wherein:

$A^1$ is independently proline, dehydroproline, pyroglutamic acid, glutamine, tyrosine, glutamic acid, 2-thiophene carboxylic acid, picolinic acid, nicotinic acid, isonicotinic acid, cyclohexane carboxylic acid, tetrahydrofuroic acid, oxothiazolidine carboxylic acid, cyclopentane carboxylic acid, thiophene carboxylic acid, tetrahydrofuran carboxylic acid, pipecolinic acid, piperidine carboxylic acid, pyrrole carboxylic acid, isopyrrole carboxylic acid, pyrazole carboxylic acid, isoimidazole carboxylic acid, triazole carboxylic acid, dithiole carboxylic acid, oxathiole carboxylic acid, isoxazole carboxylic acid, oxazole carboxylic acid, thiazole carboxylic acid, isothiazole carboxylic acid, oxadiazole carboxylic acid, oxatriazole carboxylic acid, oxathiolene carboxylic acid, oxazine carboxylic acid, oxathiazole carboxylic acid, dioxazole carboxylic acid, pyran carboxylic acid, pyrimnidine carboxylic acid, pyridazine carboxylic acid, pyrazine carboxylic acid, piperazine carboxylic acid, triazine carboxylic acid, isooxazine carboxylic acid, oxathiazene carboxylic acid, morpholine carboxylic acid, indole carboxylic acid, indolenene carboxylic acid, 2-isobenzazole carboxylic acid, 1,5-pyridine carboxylic acid, pyranol[3,4-b]pyrrole carboxylic acid, isoindazole carboxylic acid, indoxazine carboxylic acid, benzoxazole carboxylic acid, anthranil carboxylic acid, quinoline carboxylic acid, isoquinoline carboxylic acid, cinnoline carboxylic acid, benzoic acid, quinazolene carboxylic acid, naphthyridine carboxylic acid, pyrido[3,4-b]-pyridine carboxylic acid, pyrido[3,2-b]-pyridine carboxylic acid, pyrido[4,3-b] pyridine carboxylic acid, 1,3,2-benzoxazine carboxylic acid, 1,4,2-benzoxazine carboxylic acid, 2,3,1-benzoxazine carboxylic acid, 3,1,4-benzoxazine carboxylic acid, 1,2-benzisoxazine carboxylic acid, 1,4-benzisoxazine carboxylic acid, carbazole carboxylic acid, acridine carboxylic acid, purine carboxylic acid, hydroxypicolinic acid, hydantoin carboxylic acid, furan carboxylic acid, N-acetyl proline, or azetidine carboxylic acid;

$B^1$ is independently serine, threonine, glutamic acid, tyrosine, aspartic acid, hydroxyproline, O-benzyl serine, N-methyl serine, N-methyl threonine, N-methyl glutamic acid, N-methyl tyrosine, N-methyl aspartic acid, 2-amino-3-hydroxythiopropanoic acid, 2-amino-1-hydroxypropyl or 2-amino-1-hydroxypent-3-enyl;

$X^1$ is O, S, $NR_1$ or $CR_2R_3$;

$Y^1$ is heteroaryl, O, S, $NR_1$, $CR_2R_3$, aryl, $C_{2-5}$ alkyl, $C_{2-5}$ alkenyl, or $C_{2-5}$ alkynyl, napthyl, xylyl, $CON(R_3)$, piperazine, biphenyl, diacetylene benzene or divinyl benzene;

$R_1$, $R_2$ and $R_3$ are independently hydrogen, $C_{1-4}$ alkyl, $C_{2-4}$ alkenyl or $C_{2-4}$ alkynyl, $C_{3-7}$ cycloalkyl, heteroaryl or aryl, all of which may be substituted by one or more $C_{1-3}$ alkyl groups;

m and n are independently 0 to 5;

r is 0 to 2;

s is 0 or 1;

or a pharmaceutically acceptable salt thereof.

The compounds of this invention are also illustrated by Formula (II):

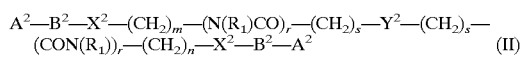

wherein:

$A^2$ is independently 3-aminopyrazole, 5-aminopyrazole, aminothiazole, aminopyrimidine, aminothiadiazole, aminopyridazine, 2-aminopyridine, 3-aminopyridine, 4-aminopyridine, aminopurine, aminopteridine, 3-aminoisoxazole, 5-aminoisoxazole, 3-amino-1,2,4-triazine, 2-amino-1,3,5-triazine, aminodimethyluracil, aminomethyluracil, 2-amino-3-hydroxypyridine, 2-amino-4-hydroxpyridine, 3-(aminomethyl)pyridine, 4-(aminomethyl)pyridine, aniline, 3-aminopyrrolidine, aminoquinoline, aminotetrazole, 3-amino- 1,2,4-triazole, 5-aminouracil, 6-aminouracil, aminopyrrole, aminofuran, aminothiophene, 3-aminopiperidine, 4-aminopiperidine, cyclohexylamine, cyclopentylamine, pyrazolo [3,4-b] pyridine, 3-aminobutyrolactam or 2-aminocyclopentanone;

$B^2$ is independently serine, threonine, glutamic acid, tyrosine, aspartic acid, hydroxyproline, O-benzyl serine, N-methyl serine, N-methyl threonine, N-methyl glutamic acid, N-methyl tyrosine, or N-methyl aspartic acid;

$X^2$ is CO, CS or $CR_2R_3$;

$Y^2$ is heteroaryl, O, S, $NR_1$, $CR_2R_3$, aryl, $C_{2-5}$ alkyl, $C_{2-5}$ alkenyl, $C_{2-5}$ alkynyl, napthyl, xylyl, $CON(R_3)$, piperazine, biphenyl, diacetylene benzene or divinyl benzene;

$R_1$, $R_2$ and $R_3$ are independently hydrogen, $C_{1-4}$ alkyl, $C_{2-4}$ alkenyl, or $C_{2-4}$ alkynyl, $C_{3-7}$ cycloalkyl, heteroaryl or aryl, all of which may be substituted by one or more $C_{1-3}$ alkyl groups;

m and n are independently 0 to 5;

r is 0 to 2;

s is 0 or 1;

or a pharmaceutically acceptable salt thereof.

In Formula II, $A^2$ and $B^2$ are connected via an amide bond, synthesized by condensing the amino group of $A^2$ and the carboxyl group of $B^2$.

"Aryl" means an aromatic ring or ring system of 5–10 carbon atoms, such as phenyl, benzyl, phenethyl, or naphthyl. Preferably the aryl is monocyclic, i.e., phenyl.

"Heteroaryl" means an aromatic ring system containing one or more heteroatoms, such as imidazolyl, triazolyl, oxazolyl, pyridyl, pyrimidyl, pyrazolyl, pyrrolyl, furanyl, or thienyl.

All alkyl, alkenyl, alkynyl and alkoxy groups may be straight or branched. The term "halogen" is used to mean iodo, fluoro, chloro or bromo. Alkyl groups may be substituted by one or more halogens up to perhalogenation.

The compounds of the present invention may contain one or more asymmetric carbon atoms and may exist in racemic and optically active form. All of these compounds and diastereoisomers are contemplated to be within the scope of the present invention.

Also included in this invention are pharmaceutically acceptable salt complexes of the compounds of this invention.

Preferred compounds of Formula I are those in which:

$A^1$ is pyroglutamic acid, picolinic acid, proline, pipecolinic acid, dehydroproline, azetidine carboxylic acid, or pyrole carboxylic acid;

$B^1$ is glutamic acid, serine, aspartic acid or N-methyl serine;

$X^1$ is $NR_1$;

m and n are 1 or 2;

$Y^1$ is phenyl or xylyl.

r is 1 s is 0

Especially preferred are:

N,N'-Bis(picolinyl-seryl-β-alanyl)-1,4-diaminobenzene;

N,N'-Bis(pyroglutamyl-glutamyl-β-alanyl)-1,4-diaminobenzene; and

N,N'-Bis(dehydroprolyl-seryl-β-alanyl)-1,4-diaminobenzene.

N,N'-Bis(picolinoyl-seryl-glycol)-1,4-diaminoxylene

N,N'-Bis(prolyl-seryl-β-alanyl)-1,4-diaminobenzene

N,N'-Bis(azetidinyl-seryl-β-alanyl)-1,4-diaminobenzene

N,N'-Bis(picolinoyl-N-methylseryl-β-alanyl)-1,4-diaminobenzene

N,N'-Bis(pyrrolyl-seryl-β-alanyl)-1,4-diaminobenzene

Preferred compounds of Formula II are those in which:

$A^2$ is 2-aminopyridine;

$B^2$ is serine;

$X^2$ is CO;

m and n are 2;

s is 0;

$Y^2$ is phenyl; and r is 1.

The present invention provides compounds of Formula (I) which can be prepared by a process which comprises:

a) where r is 1; m and n are equivalently 0 to 5; $X^1$ is O, S or $NR_1$; s is 0 or 1 and $R^1$ and $Y^1$ are as defined in Formula (I); reacting a compound of Formula (2):

$$H(R_1)N-(CH_2)_s-Y^1-(CH_2)_s-N(R_1)H \quad (2)$$

wherein $R_1$ and $Y^1$ are as defined in Formula (I) with a suitably protected carboxylic acid of Formula (3):

$$HX^1-(CH_2)_m-CO_2H \quad (3)$$

wherein $X^1$ is O, S or $NR_1$; and m is 0 to 4; using standard coupling reagents such as EDC/HOBt in a suitable solvent such as N,N-dimethylformamide to provide a compound of Formula (4):

$$HX^1-(CH_2)_m-CON(R_1)-(CH_2)_s-Y^1-(CH_2)_s-N(R_1)CO-(CH_2)_m-X^1H \quad (4)$$

Compound (4) is reacted with a suitably protected $B^1$ wherein $B^1$ is as defined in Formula (I), using standard coupling reagents such as EDC/HOBt in a suitable solvent such as N,N-dimethylformamide to provide a compound of Formula (5):

$$B^1-X^1-(CH_2)_m-CON(R_1)-(CH_2)_s-Y^1-(CH_2)_s-N(R_1)CO-(CH_2)_m-X^1-B^1 \quad (5)$$

Compound (5) is then reacted with $A^1$ wherein $A^1$ is as defined in Formula (I), using standard coupling reagents such as EDC/HOBt in a suitable solvent such as N,N-dimethylformamide. Removal of the protecting groups with anhydrous hydrogen fluoride gives compounds of Formula (I).

b) Alternatively, a compound of Formula (I) wherein r is 1; s is 0 or 1; m and n are independently but not equivalently 0 to 5; $X^1$ is O, S or $NR_1$; and $R_1$ and $Y^1$ are as defined in Formula (I);

can be prepared by a process which comprises reacting a compound of Formula (6):

$$H(R_1)N-(CH_2)_s-Y^1-(CH_2)_s-N(R_1)P \quad (6)$$

wherein $R_1$ and $Y^1$ are as defined in Formula (I) and P is a suitable protecting group such as t-butyl carbamate, with a suitably protected carboxylic acid of Formula (3), using standard coupling reagents such as EDC/HOBt in a suitable solvent such as N,N-dimethylformamide to provide a compound of Formula (7):

$$HX^1-(CH_2)_m-CON(R_1)-(CH_2)_s-Y^1-(CH_2)_s-N(R_1)P \quad (7)$$

Protecting group P is cleaved by a suitable reagent such as trifluoroacetic acid from compound (7) which is further reacted with a suitably protected carboxylic acid of Formula (8):

$$HX^1-(CH_2)_n-CO_2H \quad (8)$$

wherein $X^1$ is O, S or $NR_1$; and n is defined as in Formula (I), using standard coupling reagents such as EDC/HOBt in a suitable solvent such as N,N-dimethylformamide to provide a compound of Formula (9):

$$HX^1-(CH_2)_m-CON(R_1)-(CH_2)_s-Y^1-(CH_2)_s-N(R_1)CO-(CH_2)_n-X^1H \quad (9)$$

Compound (9) is reacted with a suitably protected $B^1$, wherein $B^1$ is as defined in Formula (I), using standard coupling reagents such as EDC/HOBt in a suitable solvent such as N,N-dimethylformamide to provide a compound of Formula (10):

$$B^1-X^1-(CH_2)_m-CON(R_1)-(CH_2)_s-Y^1-(CH_2)_s-N(R_1)CO-(CH_2)_n-X^1-B^1 \quad (10)$$

Compound (10) is reacted with $A^1$ wherein $A^1$ is as defined in Formula (I), using standard coupling reagents such as EDC/HOBt in a suitable solvent such as N,N-dimethylformamide. Removal of the protecting groups with anhydrous hydrogen fluoride gives compounds of Formula (I).

c) Alternatively, a compound of Formula (I) wherein r is 0; $X^1$ is O, s is 0; S or $NR_1$; $Y^1$, $R_1$, m and n are as defined in Formula (I); can be prepared by a process which comprises reacting a compound of Formula (11):

$$HX^1-(CH_2)_m-Y^1-(CH_2)_n-X^1H \quad (11)$$

wherein $X^1$ is O, S or $NR_1$ and $Y^1$, $R_1$, m and n are defined as in Formula (I); with a suitably protected $B^1$ wherein $B^1$ is as defined in Formula (I), using standard coupling reagents such as EDC/HOBt in a suitable solvent such as N,N-dimethylformamide to provide a compound of Formula (12):

$$B^1-X^1-(CH_2)_m-Y^1-(CH_2)_n-X^1-B^1 \quad (12)$$

Compound (12) is reacted with $A^1$ wherein $A^1$ is as defined in Formula (I), using standard coupling reagents such as EDC/HOBt in a suitable solvent such as N,N-dimethylformamide. Removal of the protecting groups with anhydrous hydrogen fluoride gives compounds of Formula (I).

d) Alternatively, a compound of Formula (I) wherein r is 1; m and n are equivalently 0 to 5; $X^1$ is $CR_2R_3$; $R_1$, $R_2$, $R_3$ and $Y^1$ are as defined in Formula (I); can be prepared by a process which comprises reacting a compound of Formula (2) with a carboxylic acid of Formula (13):

$$Br-X^1-(CH_2)_m-CO_2H \quad (13)$$

wherein $X^1$ is $CR_2R_3$ s is 0 or 1 and m is 0 to 5; using standard coupling reagents such as EDC/HOBt in a suitable solvent such as N,N-dimethylforrnamide to provide a compound of Formula (14):

$$Br-X^1-(CH_2)_m-CON(R_1)-(CH_2)_s-Y^1-(CH_2)_s-N(R_1)CO-(CH_2)_m-X^1-Br \quad (14)$$

The corresponding organomagnesium moiety of compound (14) is then reacted with the acid chloride of a suitably protected $B^1$ wherein $B^1$ is as defined in Formula (I), in the presence of a suitable catalyst such as copper (I) chloride, in a suitable solvent such as tetrahydrofuran to give a compound of Formula (15):

$$B^1-X^1-(CH_2)_m-CON(R_1)-(CH_2)_s-Y^1-(CH_2)_s-N(R_1)CO-(CH_2)_m-X^1-B^1 \quad (15)$$

Compound (15) is reacted with $A^1$ wherein $A^1$ is as defined in Formula (I), using standard coupling reagents such as EDC/HOBt in a suitable solvent such as N,N-dimethylformamide. Removal of the protecting groups with anhydrous hydrogen fluoride gives compounds of Formula (I).

e) Alternatively, a compound of Formula (I) wherein r is 1; m and n are independently but not equivalently 0 to 5; $X^1$ is $CR_2R_3$; and $R_1$, $R_2$, $R_3$ and $Y^1$ are as defined in Formula (I); can be prepared by a process which comprises reacting a compound of Formula (6) with a suitably protected carboxylic acid of Formula (13), using standard coupling reagents such as EDC/HOBt in a suitable solvent such as N,N-dimethylformamide to provide a compound of Formula (16):

Br—X$^1$—(CH$_2$)$_m$—CON(R$_1$)—(CH$_2$)$_s$—Y$^1$—(CH$_2$)$_s$—N(R$_1$)P  (16)

Protecting group P is cleaved by a suitable reagent such as trifluoroacetic acid from compound (16) which is further reacted with a suitably protected carboxylic acid of Formula (17):

Br—X$^1$—(CH$_2$)$_n$—CO$_2$H  (17)

wherein X$^1$ is CR$_2$R$_3$ and n is 0 to 5, using standard coupling reagents such as EDC/HOBt in a suitable solvent such as N,N-dimethylformamide to provide a compound of Formula (18):

Br—X$^1$—(CH$_2$)$_m$—CON(R$_1$)—(CH$_2$)$_s$—Y$^1$—(CH$_2$)$_s$—N(R$_1$)CO—(CH$_2$)$_n$—X$^1$—Br  (18)

The corresponding organomagnesium moiety of compound (18) is then reacted with the acid chloride of a suitably protected B$^1$ wherein B$^1$ is as defined in Formula (I), in the presence of a suitable catalyst such as copper (1) chloride, in a suitable solvent such as tetrahydrofuran to give a compound of Formula (19):

B$^1$—X$^1$—(CH$_2$)$_m$—CON(R$_1$)—(CH$_2$)$_s$—Y$^1$—(CH$_2$)$_s$—N(R$_1$)CO—(CH$_2$)$_n$—X$^1$—B$^1$  (19)

Compound (19) is reacted with A$^1$ wherein A$^1$ is as defined in Formula (I), using standard coupling reagents such as EDC/HOBt in a suitable solvent such as N,N-dimethylformamide. Removal of the protecting groups with anhydrous hydrogen fluoride gives compounds of Formula (I).

f) Alternatively, a compound of Formula (I) wherein r is 0; s is 0; X$^1$ is CR$_2$R$_3$; Y$^1$, R$_2$, R$_3$, m and n are as defined in Formula (I); can be prepared by a process which comprises reacting an organomagnesium compound of Formula (20):

BrMg—X$^1$—(CH$_2$)$_m$—Y$^1$—(CH$_2$)$_n$—X$^1$—MgBr  (20)

wherein X$^1$ is CR$_2$R$_3$ and R$_2$, R$_3$, m, n, and Y$^1$ are as defined in Formula (I), with the acid chloride of a suitably protected B$^1$ wherein B$^1$ is as defined in Formula (I), in the presence of a suitable catalyst such as copper (1) chloride, in a suitable solvent such as tetrahydrofuran to give a compound of Formula (21):

B$^1$—X$^1$—(CH$_2$)$_m$—Y$^1$—(CH$_2$)$_n$—X$^1$—B$^1$  (21)

Compound (21) is reacted with A$^1$ wherein A$^1$ is as defined in Formula (I), using standard coupling reagents such as EDC/HOBt in a suitable solvent such as N,N-dimethylformamide. Removal of the protecting groups with anhydrous hydrogen fluoride gives compounds of Formula (I).

The present invention provides compounds of Formula (II) which can be prepared by a process which comprises:

A$^2$—B$^2$—X$^2$—(CH$_2$)$_m$—(N(R$_1$)CO)$_r$—(CH$_2$)$_s$—Y$^2$—(CH$_2$)$_s$—(CON(R$_1$))$_r$—(CH$_2$)$_n$—X$^2$—B$^2$—A$^2$  (II)

a) where r is 1; m and n are equivalently 0 to 5; s is as defined in Formula (II) and X is CO; reacting A$^2$ with a suitably protected B$^2$ wherein A$^2$ and B are defined as in Formula (I), using standard coupling reagents such as EDC/HOBt in a suitable solvent such as N,N-dimethylformamide to provide a compound of Formula (22):

A$^2$—B$^2$  (22)

Compound (22) is then reacted with a compound of Formula (23):

HO—X$^2$—(CH$_2$)$_m$—N(R$_1$)P  (23)

wherein X is CO; m is 0 to 4; P is a suitable protecting group such as t-butoxycarbonyl; and R$_1$ is as defined in Formula (II); using standard coupling reagents such as EDC/HOBt in a suitable solvent such as N,N-dimethylformamide to give a compound of Formula (24):

A$^2$—B$^2$—X$^2$—(CH$_2$)$_m$—N(R$_1$)P  (24)

The protecting group P is cleaved by a suitable reagent such as trifluoroacetic acid from compound (24) and is further reacted with one half of an equivalent of a compound of Formula (25):

HO$_2$C—(CH$_2$)$_s$—Y$^2$—(CH$_2$)$_s$—CO$_2$H  (25)

wherein Y$^2$ is as defined in Formula (II); using standard coupling reagents such as EDC/HOBt in a suitable solvent such as N,N-dimethylformamide. Removal of the protecting groups with anhydrous hydrogen fluoride gives compounds of Formula (II).

b) Alternatively, a compound of Formula (II) wherein r is 1; m and n are independently but not equivalently 0 to 5; and s is as defined in Formula (II); and X$^2$ is CO; can be prepared by a process which comprises reacting a compound of Formula (24) with a compound of Formula (26):

HO$_2$C—(CH$_2$)$_s$—Y$^2$—(CH$_2$)$_s$—CO$_2$CH$_3$  (26)

in an analogous manner to (a) to give compounds of Formula (27):

A$^2$—B$^2$—X$^2$—(CH$_2$)$_m$—N(R$_1$)CO—(CH$_2$)$_s$—Y$^2$—(CH$_2$)$_s$—CO$_2$CH$_3$  (27)

The methyl ester of compound (27) is hydrolyzed using standard methods such as lithium hydroxide in aqueous tetrahydrofuran and further reacted with a compound of Formula (28):

A$^2$—B$^2$—X$^2$—(CH$_2$)$_n$—N(R$_1$)P  (28)

prepared in a manner analogous to the preparation of (24) using standard coupling reagents such as EDC/HOBt in a suitable solvent such as N,N-dimethylformamide. Removal of the protecting groups with anhydrous hydrogen fluoride gives compounds of Formula (II).

c) Alternatively, a compound of Formula (II) wherein r and s are 0; X$^2$ is CO; s, m and n are defined as in Formula (II); can be prepared by a process which comprises reacting a compound of Formula (22) with a compound of Formula (29):

HO—X$^2$—(CH$_2$)$_m$—Y$^2$—(CH$_2$)$_n$—X$^2$—OH  (29)

using standard coupling reagents such as EDC/HOBt in a suitable solvent such as N,N-dimethylformamide. Removal of the protecting groups using anhydrous hydrogen fluoride then gives compounds of Formula (II).

d) Alternatively, a compound of Formula (II) wherein r is 1; m and n are equivalently 0 to 5; X$^2$ is CR$_2$R$_3$ and R$_3$ is hydrogen; and s is as defined in Formula (II); can be prepared by a process which comprises reacting a compound of Formula (22) with a compound of Formula (30);

R$_2$—CO—(CH$_2$)$_m$—N(R$_1$)P  (30)

wherein P is a suitable protecting group such as t-butoxycarbonyl; under dehydration conditions. The resulting product is further reacted with a suitable reducing agent such as sodium cyanoborohydride to give a compound of Formula (31):

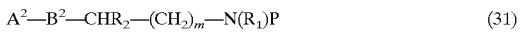
$$A^2\text{—}B^2\text{—}CHR_2\text{—}(CH_2)_m\text{—}N(R_1)P \quad (31)$$

The protecting group P is cleaved by a suitable reagent such as trifluoroacetic acid from compound (31) and is further reacted with one half of an equivalent of a compound of Formula (25) using standard coupling reagents such as EDC/HOBt in a suitable solvent such as N,N-dimethylformamide. Removal of the protecting groups with anhydrous hydrogen fluoride gives compounds of Formula (II).

e) Alternatively, a compound of Formula (II) wherein r is 1; m and n are equivalently 0 to 5; $X^2$ is $CR_2R_3$; and s is defined in Formula (II); can be prepared by a process which comprises reacting a compound of Formula (22) with a compound of Formula (30) under dehydration conditions. The resulting product is further reacted with an organometallic species of Formula (32):

$$R_3\text{—}M \quad (32)$$

wherein M is a suitable metal such as lithium and $R_3$ is as defined in Formula (II); to give a compound of Formula (33):

$$A^2\text{—}B^2\text{—}CR_2R_3\text{—}(CH_2)_m\text{—}N(R_1)P \quad (33)$$

The protecting group P is cleaved by a suitable reagent such as trifluoroacetic acid from compound (33) and is further reacted with one half of an equivalent of a compound of Formula (25) using standard coupling reagents such as EDC/HOBt in a suitable solvent such as N,N-dimethylformamide. Removal of the protecting groups with anhydrous hydrogen fluoride gives compounds of Formula (II).

f) Alternatively, a compound of Formula (II) wherein r is 1; m and n are independently but not equivalently 0 to 5; $X^2$ is $CR_2R_3$ and $R_3$ is hydrogen: and s is defined as in Formula (II); can be prepared by a process that comprises reacting a compound of Formula (31) with a compound of Formula (26) in an analogous manner to (d) to give a compound of Formula (34):

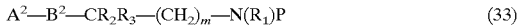
$$A^2\text{—}B^2\text{—}CR_2H\text{—}(CH_2)_m\text{—}N(R_1)CO\text{—}(CH_2)_s\text{—}Y^2\text{—}(CH_2)_s\text{—}CO_2CH_3 \quad (34)$$

The methyl ester of compound (34) is hydrolyzed using standard methods such as lithium hydroxide in aqueous tetrahydrofuran and further reacted with a compound of Formula (35):

$$A^2\text{—}B^2CR_2H\text{—}(CH_2)_n\text{—}N(R_1)P \quad (35)$$

prepared in a manner analogous to the preparation of (31) using standard coupling reagents such as EDC/HOBt in a suitable solvent such as N,N-dimethylformamide. Removal of the protecting groups with anhydrous hydrogen fluoride gives compounds of Formula (II).

g) Alternatively, a compound of Formula (II) wherein r is 1; m and n are independently but not equivalently 0 to 5; $X^2$ is $CR_2R_3$; and s is defined as in Formula (II); can be prepared by a process that comprises reacting a compound of Formula (33) with a compound of Formula (26) in an analogous manner to (d) to give a compound of Formula (36):

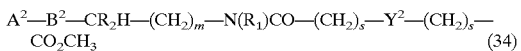
$$A^2\text{—}B^2\text{—}CR_2R_3\text{—}(CH_2)_m\text{—}N(R_1)CO\text{—}(CH_2)_s\text{—}Y^2\text{—}(CH_2)_s\text{—}CO_2CH_3 \quad (36)$$

The methyl ester of compound (36) is hydrolyzed using standard methods such as lithium hydroxide in aqueous tetrahydrofuran and further reacted with a compound of Formula (37):

$$A^2\text{—}B^2\text{—}CR_2R_3\text{—}(CH_2)_n\text{—}N(R_1)P \quad (37)$$

prepared in a manner analogous to the preparation of (33) using standard coupling reagents such as EDC/HOBt in a suitable solvent such as N,N-dimethylformamide. Removal of the protecting groups with anhydrous hydrogen fluoride gives compounds of Formula (II).

h) Alternatively, a compound of Formula (II) wherein r and s are 0; $X^2$ is $CR_2R_3$; $R_3$ is hydrogen and m and n are defined as in Formula (II); can be prepared by a process that comprises reacting a compound of Formula (22) with a compound of Formula (38):

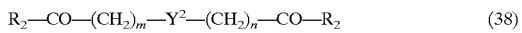
$$R_2\text{—}CO\text{—}(CH_2)_m\text{—}Y^2\text{—}(CH_2)_n\text{—}CO\text{—}R_2 \quad (38)$$

under dehydration conditions. The resulting product is further reacted with a suitable reducing agent such as sodium cyanoborohydride to give a compound of Formula (39):

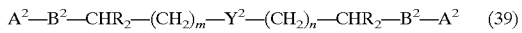
$$A^2\text{—}B^2\text{—}CHR_2\text{—}(CH_2)_m\text{—}Y^2\text{—}(CH_2)_n\text{—}CHR_2\text{—}B^2\text{—}A^2 \quad (39)$$

Removal of the protecting groups with an appropriate agent such as TFA, HF, HBr/HOAC or hydrogenation gives compounds of Formula (II).

i) Alternatively, a compound of Formula (II) wherein r and s are 0; $X^2$ is $CR_2R_3$ and m and n are defined as in Formula (II); can be prepared by a process that comprises reacting a compound of Formula (22) with a compound of Formula (38). The resulting product is further reacted with a organometallic species of Formula (32) to give a compound of Formula (40).

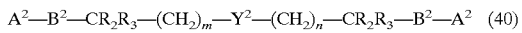
$$A^2\text{—}B^2\text{—}CR_2R_3\text{—}(CH_2)_m\text{—}Y^2\text{—}(CH_2)_n\text{—}CR_2R_3\text{—}B^2\text{—}A^2 \quad (40)$$

Removal of the protecting groups with anhydrous hydrogen fluoride gives compounds of Formula (II).

In general, in order to exert a stimulatory effect, the peptides of the invention may be administered to human patients by injection in the dose range of 50 ng to 100 mg preferably 500 ng to 50 mg, or orally in the dose range of 0.05 mg to 50 mg, for example 100 μg to 10 mg per 70 kg body weight per day; if administered by infusion or similar techniques, the dose may be in the range 0.5 ng to 10 mg per 70 kg body weight, for example about 3 micrograms over six days. In principle, it is desirable to produce a concentration of the peptide of about $10^{-13}M$ to $10^{-2}M$ in the extracellular fluid of the patient.

According to a still further feature of the present invention there are provided pharmaceutical compositions comprising as active ingredient one or more compounds of Formula (I) or Formula (II) as herein before defined or physiologically compatible salts thereof, in association with a pharmaceutical carrier or excipient. The compositions according to the invention may be presented for example, in a form suitable for oral, nasal, parenteral or rectal administration.

As used herein, the term "pharmaceutical" includes veterinary applications of the invention. These peptides may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such a glyceryl monostearate or glyceryl distearate, alone or with a wax. The amount of solid carrier varies but, preferably will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. Capsules containing one or several active ingredients may be produced, for example, by mixing the active ingredients with inert carriers, such as lactose or sorbitol, and filling the mixture into gelatin capsules. When a liquid carrier is used, the preparation will be in the form of a syrup, elixir, emulsion or an aqueous or non-aqueous suspension. Such a liquid formulation may be administered directly p.o. or filled into a soft gelatin capsule. Organ specific carrier systems may also be used.

Alternately pharmaceutical compositions of the peptides of this invention, or derivatives thereof, may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration and contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

For rectal administration, a pulverized powder of the peptides of this invention may be combined with excipients such as cocoa butter, glycerin, gelatin or polyethylene glycols and molded into a suppository. The pulverized powders may also be compounded with an oily preparation, gel, cream or emulsion, buffered or unbuffered, and administered through a transdermal patch.

Nasal sprays may be formulated similarly in aqueous solution and packed into spray containers either with an aerosol propellant or provided with means for manual compression.

Dosage units containing the compounds of this invention preferably contain 0.05–50 mg, for example 0.05–5 mg of the peptide of formula (I) or (II) or salt thereof.

According to a still further feature of the present invention there is provided a method of inhibition of myelopoiesis which comprises administering an effective amount of a pharmaceutical composition as hereinbefore defined to a subject.

No unacceptable toxicological effects are expected when compounds of the invention are administered in accordance with the present invention.

The biological activity of the compounds of Formula (I) and (II) are demonstrated by the following tests.

Induction of Colony Stimulating Activity by Stromal Cells

The murine bone marrow stromal cell line, C6, is grown to confluency in plastic tissue culture dishes in RPMI-1640 medium and 5% FBS. On the day prior to the experiment this medium is changed to DMEM without added serum. To these cultures, the compounds are added in dose range of 0.1 picogram/ml to 100 microgram/ml for one hour, then washed from the cultures. The medium is replaced with fresh DMEM and the cells are incubated for 24 hours at 37° C., 5% $CO_2$. After 24 hours the C6 cell culture supernatant is collected, sterile filtered, and frozen until it can be assayed for the presence of hematopoietic colony stimulating activity (CSA) as set forth below.

Soft Agar Assay

Bone marrow cells are obtained from Lewis rats. They are adjusted to $10^6$ cells/ml in DMEM without serum. A single layer agar system utilizing the following is used: DMEM enriched with nutrients ($NaHCO_3$, pyruvate, amino acids, vitamins, and HEPES buffer); 0.3% Bacto agar, and 20% Lewis rat serum. To this are added dilutions of C6 cell line supernatant (10–2.5%) from above along with rat bone marrow cells (final concentration=$10^5$ cells/ml). The agar plates are incubated at 37° C., 5% $CO_2$ for 7–8 days. Colonies of proliferating bone marrow cells (CFU-C) are counted utilizing a microscope. The number of agar colonies counted is proportional to the amount of CSA present within the C6 bone marrow stromal cell line supernatant.

Herpes Simplex Mouse Model

Seven days prior to infection, Balb/c mice are injected intraperitoneally once a day with a 0.2 ml volume at doses of 1, 10 and 100 micrograms/kg of compound. Control mice receive injections of 0.1 ml of a mixture of the dilution buffer, DPBS and 0.5% heat inactivated normal mouse serum.

The mice are infected with a Herpes Simplex virus (strain MS) by injecting $5.0 \times 10^5$/pfu suspended in 0.05 mls of PBS in each rear foot pad. The mice continue to get compound or control injections until moribund (unable to get food or water). Usually paralysis of the hind leg occurs approximately eight days after infection. The paralysis progresses until encephalitis occurs.

Alternatively, the virus is inoculated by means of a vaginal route. A cotton plug containing $5.0 \times 10^5$/pfu of the MS-NAP strain is inserted into the vagina of the mouse.

A Wilcoxin test is used to determine if a significant increase in survival is found in the treated verses contol group.

Candida Challenge

Candida albicans strain B311a is used. This strain has been mouse passed then frozen at $-70°$ C. B311a is virulent to immunosuppressed mice in the range of 5.0 to $8.0 \times 10^4$ cfu/mouse and for normal mice in the range of 1.0 to $2.0 \times 10^5$ cfu/mouse. A sample from the frozen stock of Candida was grown on Sabouroud dextrose slants and then transferred to 50 ml. shake cultures of Sabouroth broth for 18 hours. The cells were washed three times, then counted by hemocytometer, and viability was confirmed by methylene dye exclusion. Viability counts were performed on the inoculum to confirm the counts.

All mice (Balb/c) infected with Candida were infected i.v. with cells suspended in 0.2 mls. of saline. Some mice are sublethally myelodepressed with 300 rads of irradiation. Beginning 2 hours following irradiation, the animals are injected with compound at a dose range of 10 ng/kg to 100 micrograms/kg using CSF as a positive control, or excipient, daily. Seven days after irradiation and treatment begins, the mice are challenged with Candida albicans by intravenous administration. Note that this represents approximately a LD75 for normal mice. In other studies the mice are not immunosuppressed. In these studies the mice are treated starting seven days post infection in the same manner as the irradiated mice. In both models the mice are followed until moribund and the change is survival compared using the Wilcoxin test.

The examples which follow serve to illustrate this invention. The examples are intended to in no way limit the scope of this invention, but are provided to show how to make and use the compounds of this invention.

In the examples, all temperatures are in degrees Centigrade.

The abbreviations and symbols commonly used in the art are used herein to describe the peptides and reagents used in their synthesis.

Ala=alanine
Apy=2-aminopyridine
Asp=aspartic acid
Cys=cysteine
DCU=dicyclohexylurea
DCC=dicyclohexylcarbodiimide
Glu=glutamic acid
$HOB_t$=1 hydroxybenzyltriazole
$(Pr)_2NEt$=diisopropylethylamine
NMM=N-methylmorpholine
PyBOP=benzotriazol-1-yloxy-tripyrrolidino phosphonium hexafluorophosphate
Ser=serine
tyr=tyrosine

EXAMPLE 1

N,N'-Bis(picolinoyl-seryl-β-alanyl)-1,4-diaminobenzene

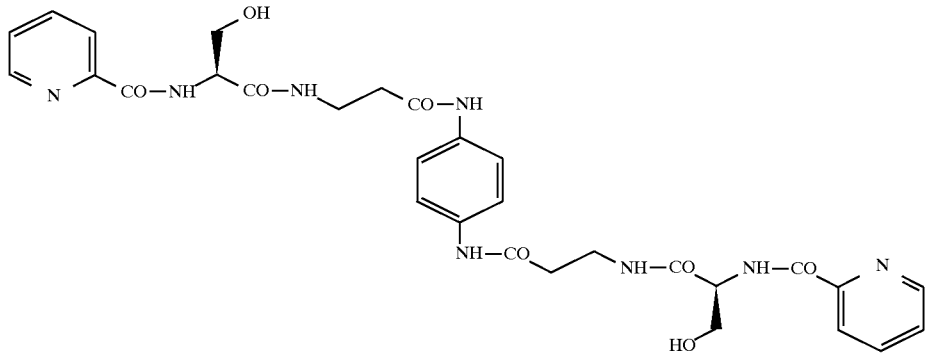

a) N,N'-Bis(BOC-β-alanyl)-1,4-diaminobenzene

To 1,4-phenylenediamine dihydrochloride (0.500 g, 2.76 mmol) in $CH_2Cl_2$ (15 mL) was added $EtNiPr_2$ (1.06 mL, 6.08 mmol) followed by BOC-β-Ala (1.15 g, 6.08 mmol), HOBt (0.820 g, 6.07 mmol) and EDC (1.16 g, 6.05 mmol). The reaction mixture was allowed to stir at room temperature for 48 h. The reaction was quenched by pouring into water (50 mL) at which point a precipitate was observed. This was collected, washed with ice cold 1N HCl (50 mL) and dried under vacuum to give a white powder (0.95 g, 76%).

MS(ES+) m/z 451.2 ($MH^+$).

b) N,N'-Bis(BOC-seryl(Bzl)-β-alanyl)-1,4-diaminobenzene

To N,N'-bis(BOC-β-alanyl)-1,4-diaminobenzene (0.940 g, 2.09 mmol) in $CH_2Cl_2$ (25 mL) was added TFA (5 mL). The reaction was stirred at room temperature for 1 h. The solvent was removed in vacuo and the residue was dissolved in $CH_2Cl_2$ (25 mL). $EtNiPr_2$ (4.00 mL, 23.0 mmol), BOC-Ser(Bzl) (1.36 g, 4.61 mmol), HOBt (0.620 g, 4.59 mmol) and EDC (0.880 g, 4.59 mmol) were sequentially added. After 21 h at room temperature, the reaction was quenched by pouring into 1N HCl/brine (50 mL, 1:1 v/v) and extracted with $Et_2O$ (3×50 mL). The combined organic layers were washed with 1N HCl (20 mL), brine (20 mL) and concentrated to give a white solid (2.92 g).

c) N,N'-Bis(picolinoyl-seryl(Bzl)-β-alanyl)-1,4-diaminobenzene

To N,N'-bis(BOC-seryl(Bzl)-β-alanyl)-1,4-diaminobenzene (2.92 g crude from (b), 2.09 mmol) in $CH_2Cl_2$ (25 mL) was added TFA (5 mL). The solvent was removed in vacuo after 1 h and the residue was redissolved in $CH_2Cl_2$ (25 mL). $EtNiPr_2$ (4.00 mL, 22.9 mmol), picolinic acid (0.570 g, 4.63 mmol), HOBt (0.620 g, 4.59 mmol) and EDC (0.890 g, 4.64 mmol) were sequentially added. After 2 days at room temperature, the reaction mixture was poured into water (50 mL). The resulting precipitate was collected, washed with $Et_2O$ (20 mL), water (50 mL) and dried under vacuum to give a yellow solid (1.17 g).

A portion of the crude material (0.18 g) was purified by flash chromatography (5% to 10% MeOH/EtOAc, silica gel) to give a white solid (0.03 g).

MS (ES+) m/z 815.4 ($MH^+$).

d) N,N'-Bis(picolinoyl-seryl-β-alanyl)-1,4-diaminobenzene

An HF vessel was charged with N,N'-bis(picolinoyl-seryl (Bzl)-β-alanyl)-1,4-diaminobenzene (68.9 mg, 85.0 mmol). Anhydrous HF(ca. 5 mL) was condensed into the vessel at −78° C. which was then sealed and warmed to 0° C. After 1 h at 0° C., the HF was removed in vacuo. The residue was then dissolved in 20% MeOH/EtOAc and neutralized with solid $NaHCO_3$ (pH≈8). Removal of solvent gave a white residue which was subjected to flash chromatography (20% MeOH/EtOAc, silica gel) to give 26.0 mg (48%) of the title compound as a white solid.

$^1$H NMR (400 MHz, DMSO-$d_6$) δ9.85 (s, 2H), 8.67 (d, J=7.5 Hz, 4H), 8.21 (m, 2H), 8.03 (m, 4H), 7.64 (m, 2H), 7.46 (s, 4H), 7.37 (s, 2H), 4.46 (m, 2H) 3.73 (dd, J=13.9, 5.6 Hz, 2H), 3.66 (dd, J=11.1, 5.6 Hz, 2H), 3.36 (m, 4H), 2.45 (m, 4H).

MS (ES+) m/z 635.2 ($MH^+$); MS (ES−) m/z 633 (M-H).

EXAMPLE 2

N,N'-Bis(picolinoyl-seryl-glycyl)-1,4-diaminobenzene

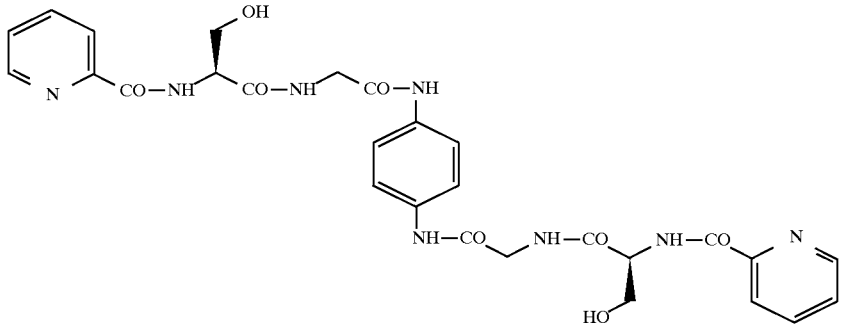

a) N,N'-Bis(BOC-glycyl)-1,4-diaminobenzene

To a suspension of 1,4-diarninobenzene dihydrochloride (0.500 g, 2.76 mmol) in $CH_2Cl_2$ (15 mL) was added sequentially $EtNiPr_2$ (1.06 mL, 6.08 mmol), BOC-Gly (1.06 g, 6.05 mmol), HOBt (0.820 g, 6.07 mmol) and EDC (1.16 g, 6.05 mmol). After 2 days at room temperature, the reaction was quenched by pouring into water (50 mL). The resulting precipitate was collected, washed with water (50 mL) and dried under vacuum to give a white solid (0.97 g, 83%).

MS (ES+) m/z 423.2 (MH$^+$).

b) N,N'-Bis(BOC-seryl(Bzl)-glycyl)-1,4-diaminobenzene

To N,N'-bis(BOC-glycyl)-1,4-diaminobenzene (0.950 g, 2.25 mmol) in $CH_2Cl_2$ (25 mL) was added TFA (5 mL). After 1 h at room temperature the solvent was removed in vacuo. The residue was dissolved in $CH_2Cl_2$ (25 mL) and $EtNiPr_2$ (4.30 mL, 25.0 mmol), BOC-Ser(Bzl) (1.46 g, 4.95 mmol), HOBt (0.670 g, 4.96 mmol) and EDC (0.950 g, 4.96 mmol) were added sequentially. After 23 h at room temperature, the reaction was quenched by pouring into brine (50 mL) and extracted with $Et_2O$ (3×50 mL). The combined organic portions were washed with 1N HCl (25 mL), brine (25 mL) and concentrated to give a yellow residue (3.42 g).

c) N,N'-Bis(picolinoyl-seryl(Bzl)-glycyl)-1,4-diaminobenzene

To a solution of N,N'-bis(seryl(Bzl)-glycyl)-1,4-diaminobenzene (3.42 g, crude from (b), 2.25 mmol) in $CH_2Cl_2$ (25 mL) was added TFA (5 mL). After 1 h at room temperature, the solvent was removed in vacuo. The residue was dissolved in $CH_2Cl_2$ (25 mL) and $EtNiPr_2$ (4.30 mL, 24.7 mmol), picolinic acid (0.610 g, 4.95 mmol), HOBt (0.670 g, 4.96 mmol) and EDC (0.950 g, 4.96 mmol) were sequentially added. After 2 days, the reaction was quenched by pouring into water (50 mL). The resulting precipitate was collected, washed with water (20 mL) and dried under vacuum to give an off-white solid (1.50 g).

A portion of the crude material (0.50 g) was subjected to flash chromatography (5% to 10% MeOH/EtOAc, silica gel) to obtain a white solid (0.15 g).

MS (ES+) m/z 787.2 (MH$^+$).

d) N,N'-Bis(picolinoyl-seryl-glycyl)-1,4-diaminobenzene

An HF vessel was charged with N,N'-bis(picolinoyl-seryl(Bzl)-glycyl)-1,4-diamninobenzene (41.2 mg, 52.0 μmol). Anhydrous HF (ca. 5 mL) was condensed into the vessel at −78° C. The reaction vessel was then sealed and warmed to 0° C. After 1 h, the HF was removed in vacuo, the residue dissolved in 20% MeOH/EtOAc and made neutral with $NaHCO_3$ (pH≈8). Removal of solvent gave a white solid which was subjected to flash chromatography (20% MeOH/EtOAc, silica gel) to give 14 mg (44%) of the title compound as a white solid.

$^1$H NMR (400 MHz, DMSO-d$_6$) δ9.71 (s, 2H), 8.80 (d, J=8.1 Hz, 2H), 8.68 (d, J=5.4 Hz, 2H), 8.54 (m, 2H), 8.06 (m, 4H), 7.65 (m, 2H), 7.55 (s, 4H), 5.31 (m, 2H), 4.55 (m, 2H), 3.91 (d, J=5.4 Hz, 4H), 3.89 (m, 2H), 3.80 (m, 2H)

MS (ES+) m/z 607.2 (MH$^+$); MS (ES−) m/z 605.2 (M-H).

EXAMPLE 3

N,N'-Bis(picolinoyl-seryl)-1,4-diaminobutane

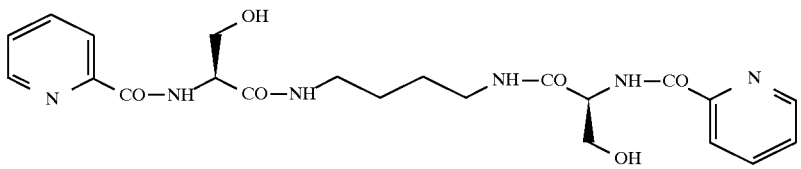

a) N,N'-Bis(seryl(Bzl))-1,4-diaminobutane

To a solution of 1,4-diaminobutane (0.500 mL, 4.97 mmol) in $CH_2Cl_2$ (50 mL) was added BOC-Ser(Bzl) (3.23 g, 10.9 mmol), HOBt (1.48 g, 10.9 mmol), $EtNiPr_2$ (1.91 mL, 10.9 mmol) and EDC (2.10 g, 10.9 mmol). After 2 days at room temperature, the reaction was diluted with $Et_2O$ (100 mL), washed with 1N HCl (20 mL), sat. $NaHCO_3$ (20 mL), brine (20 mL) and dried over $Na_2SO_4$. Concentration gave a white foam (8.19 g).

A portion of the crude material (2.00 g) was subjected to flash chromatography (30% EtOAc/hexane, silica gel) to give a white solid (0.39 g).

MS (ES+) m/z 643.0 (MH$^+$); MS (ES−) m/z 687.2 (M+HCOO$^-$).

b) N,N'-Bis(picolinoyl-seryl(Bzl))-1,4-diaminobutane

To a solution of N,N'-bis(seryl(Bzl))-1,4-diaminobutane (0.23 g, 0.36 mmol) in $CH_2Cl_2$ (5 mL) was added TFA (1 mL). After 1 h at room temperature, the solvent was removed in vacuo. The residue was dissolved in $CH_2Cl_2$ (5 mL) and EtNiPr$_2$ (0.20 mL, 1.2 mmol), picolinic acid (0.10 g, 0.81 mmol), HOBt (0.11 g, 0.81 mmol) and EDC (0.16 g, 0.81 mmol) were added sequentially. After 17 h at room temperature, the reaction was quenched by pouring into brine (20 mL) and extracting with Et$_2$O (3×50 mL). The combined organic portions were dried over Na$_2$SO$_4$ and concentrated to give a clear residue (0.33 g). Flash chromatography (5% to 20% MeOH/EtOAc, silica gel) gave 0.12 g (51%) of the desired compound as a clear oil.

MS (ES+) m/z 653.2 (MH$^+$); MS (ES−) m/z 651 (M-H).

c) N,N'-Bis(picolinoyl-seryl)-1,4-diaminobutane

An HF vessel was charged with N,N'-bis(picolinoyl-seryl (Bzl))-1,4-diantinobutane (33.0 mg, 50.6 μmol). Anhydrous HF (ca. 5 mL) was condensed into the vessel at −78° C. The vessel was sealed and the reaction warmed to 0° C. After 1 h at 0° C., the HF was removed in vacuo. The residue was taken up in 20% MeOH/EtOAc and made neutral (pH≈8) with NaHCO$_3$. Removal of solvent gave a white residue. Flash chromatography (20% MeOH/EtOAc, silica gel) gave 10 mg (42%) of the title compound.

$^1$H NMR (400 MHz, MeOH-d$_4$) δ8.64 (d, J=4.3 Hz 2H), 8.09 (d, J=7.9 Hz, 2H), 7.95 (dt, J=8.3, 7.1 Hz, 7.56 (dd, J=7.6, 4.7 Hz, 2H), 4.56 (t, J=4.8 Hz, 2H), 3.94 (dd, J=11.5, 4.9 Hz, 2H), 3.84 (dd, J=11.1, 4.9 Hz, 2H), 3.30 (m, 4H), 1.55 (m, 4H)

MS (ES+) m/z 473.2 (MH$^+$); MS (ES−) m/z 471.0 (M-H).

EXAMPLE 4

N,N'-Bis(picolinoyl-seryl)-1,4-diaminobenzene

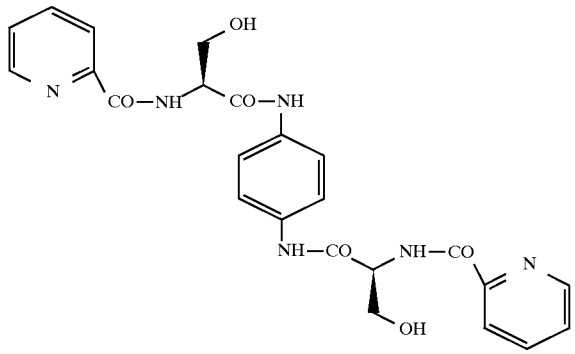

a) N,N'-Bis(BOC-seryl(Bzl))-1,4-diaminobenzene

To a suspension of 1,4-diaminobenzene dihydrochloride (0.500 g, 2.76 mmol) and BOC-Ser(Bzl) (1.79 g, 6.07 mmol) in CH$_2$Cl$_2$ (15 mL) at 0° C. was added EtNiPr$_2$ (1.06 mL, 6.08 mmol). This was followed by DCC (1.25 g, 6.07 mmol) and DMAP (0.820 g, 6.71 mmol). After 22 h at room temperature, the reaction was diluted with Et$_2$O (50 mL) and filtered through a pad of celite. The celite was rinsed with additional Et$_2$O (100 mL). The combined organic portions were concentrated in vacuo to give an off-white solid (2.43 g). Flash chromatography (5% MeOH/EtOAc, silica gel) gave 1.06 g (58%) of the desired compound as a white solid.

MS (ES+) m/z 663.2 (MH$^+$).

b) N,N'-Bis(picolinoyl-seryl(Bzl))-1,4-diaminobenzene

To a solution of N,N'-bis(BOC-seryl(Bzl))-1,4-diaminobenzene (0.47 g, 0.71 mmol) in CH$_2$Cl$_2$ (10 mL) was added TFA (2 mL). After 1.5 h at room temperature, the solvent was removed in vacuo. The residue was redissolved in CH$_2$Cl$_2$ (10 mL) and EtNiPr$_2$ (0.54 mL, 2.1 mmol), picolinic acid (0.19 g, 1.5 mmol), HOBt (0.21 g, 1.5 mmol) and DCC (0.32 g, 1.5 mmol) were added sequentially. After 18 h, the reaction was diluted with Et$_2$O (50 mL) and filtered through a pad of celite. The celite was further rinsed with Et$_2$O (50 mL) and the combined organic portions were concentrated to give an orange oil (1.54 g). Flash chromatography (10% MeOH/EtOAc, silica gel) gave 0.51 g (quantitative) of the desired compound as a white solid.

MS (ES+) m/z 673.2 (MH$^+$); MS (ES−) m/z 671.2 (m-H).

c) N,N'-Bis(picolinoyl-seryl)-1,4-diaminobenzene

An HF vessel was charged with N,N'-bis(picolinoyl-seryl (Bzl))-1,4-diaminobenzene (0.108 g 0.161 mmol). Anhydrous HF (ca. 5 mL) was condensed into the vessel at −78° C. The reaction vessel was sealed and warmed to 0 ° C. After 1 h, the HF was removed in vacuo, the residue dissolved in 20% MeOH/EtOAc and neutralized with NaHCO$_3$. This was concentrated to give a white solid (0.229 g).

A portion of the crude material (0.15 g) was subjected to flash chromatography (5% MeOH/EtOAc, silica gel) to give 14.0 mg of pure product as a white solid.

$^1$H NMR (400 MHz, DMSO-d$_6$) δ10.13 (s, 2H), 8.76 (d, J=8.0 Hz, 2H), 8.71 (d, J=4.4 Hz, 2H), 8.05 (m, 4H), 7.65 (m, 2H), 7.56 (s, 4H), 4.66 (m, 2H). 3.85 (dd, J=11.1, 4.9 Hz, 2H), 3.78 (dd, J=11.1, 4.8 Hz, 2H)

MS (ES+) m/z 493.0 (MH$^+$); MS (ES−) m/z 491.0 (M-H).

EXAMPLE 5

N,N'-Bis(nicotinoyl-seryl-β-alanyl)-1,4-diaminobenzene

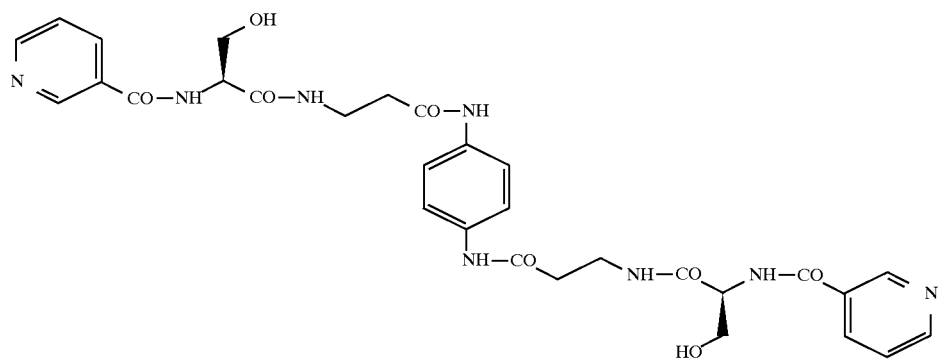

a) N,N'-Bis(nicotinoyl-seryl(Bzl)-β-alanyl)-1,4-diaminobenzene

To a solution of N,N'-bis(BOC-seryl(Bzl)-β-alanyl)-1,4-diaminobenzene (0.39 g) prepared as in Example 1, in CH$_2$Cl$_2$ (15 mL) was added TFA (15 mL). After stirring for 1 hr at room temperature, the mixture was concentrated in vacuo. The residue was azeotroped with toluene (ca. 2 mL). The resulting white solid was taken up in CH$_2$Cl$_2$ (2 mL) and EtNiPr$_2$ (0.65 mL, 3.7 mmol) was added. A portion (1.3 mL) of the resulting solution was added to a solution of nicotinoyl chloride hydrochloride (0.11 g, 0.63 mmol) in CH$_2$Cl$_2$ (1 mL) at 0° C. The reaction was warmed to room temperature. After 18 h, the reaction was quenched by pouring into a mixture of 5% Na$_2$CO$_3$ in brine (100 mL) and Et$_2$O (50 mL). The resulting precipitate was collected, washed with Et$_2$O and dried under vacuum to yield a white powder (0.20 g).

A portion of the crude material was purified by flash chromatography (20% MeOH/EtOAc, silica gel) to give a white powder (40 mg).

MS (ES+) m/z 815.2 (MH$^+$).

b) N,N'-Bis(nicotinoyl-seryl-β-alanyl)-1,4-diaminobenzene

An HF vessel was charged with N,N'-bis(nicotinoyl-seryl(Bzl)-β-alanyl)-1,4-diaminobenzene (38.1 mg, 46.8 mmol) and p-cresol (0.5 mL). Anhydrous HF (5 mL) was condensed into the vessel at −78° C. which was then sealed and warmed to 0° C. After 1 h, the HF was removed in vacuo. The residue was partitioned between Et$_2$O (75 mL) and H$_2$O (25 mL). The organic phase was extracted with H$_2$O (25 mL) and 0.1N AcOH (25 mL). The combined aqueous extracts were concentrated in vacuo to ca. ⅓ its original volume. The remaining solution was lyophilized to yield a white powder (25.8 mg). Reverse phase preparative HPLC (5% to 20% CH$_3$CN/H$_2$O (0.1% TFA), Hamilton PRP-1 HPLC prep column) gave the title compound (21.1 mg).

MS (ES+) m/z 635.2 (MH$^+$).

EXAMPLE 6

N,N'-Bis(isonicotinoyl-seryl-β-alanyl)-1,4-diaminobenzene a) N,N'-Bis(isonicotinoyl-seryl(Bzl)-β-alanyl )-1,4-diaminobenzene To a solution of N,N'-bis(BOC-seryl(Bzl)-β-alanyl)-1,4-diaminobenzene (0.38 g) as prepared in Example 1, in CH$_2$Cl$_2$ (15 mL) was added TFA (15 mL). After stirring for 1 hr at room temperature, the mixture was concentrated in vacuo. The residue was azeotroped with toluene (ca. 2 mL). The resulting oil was taken up in DMF(2 mL) and EtNiPr2 (0.65 mL, 3.7 mmol) was added. A portion (1.3 mL) of this solution was added to a solution of isonicotinoyl chloride hydrochloride (0.12 g, 0.66 mmol) in CH$_2$Cl$_2$ (1 mL) at 0° C. The reaction was warmed to room temperature. After 18 h, the reaction was quenched by pouring into a mixture of 5% Na$_2$CO$_3$ in brine (100 mL) and Et$_2$O (50 mL). The resulting precipitate was collected, washed with Et$_2$O and dried under vacuum to yield a white powder (0.20 g).

A portion of the crude material was purified by flash chromatography (20% MeOH/EtOAc, silica gel) to give a white powder (33 mg).

MS (ES+) m/z 815.2 (MH$^+$).

b) N,N'-Bis(isonicotinoyl-seryl-β-alanyl)-1,4-diaminobenzene

An HF vessel was charged with N,N'-bis(isonicotinoyl-seryl(Bzl)-β-alanyl)-1,4-diaminobenzene (33.4 mg, 41.0 mmol) and p-cresol (0.5 mL). Anhydrous HF (5 mL) was condensed into the vessel at −78° C. which was then sealed and warmed to 0° C. After 1 h, the HF was removed in vacuo. The residue was partitioned between Et$_2$O (75 mL) and H$_2$O (25 mL). The organic phase was extracted with H$_2$O (25 mL) and 0.1N AcOH (25 mL). The combined aqueous extracts were concentrated in vacuo to ca. ⅓ its original volume. The remaining solution was lyophilized to yield a white powder (13.2 mg). Reverse phase preparative HPLC (5% to 20% CH$_3$CN/H$_2$O (0.1% TFA), Hamilton PRP-1 HPLC prep column) gave the title compound (3.7 mg).

MS (ES+) m/z 635.2 (MH$^+$).

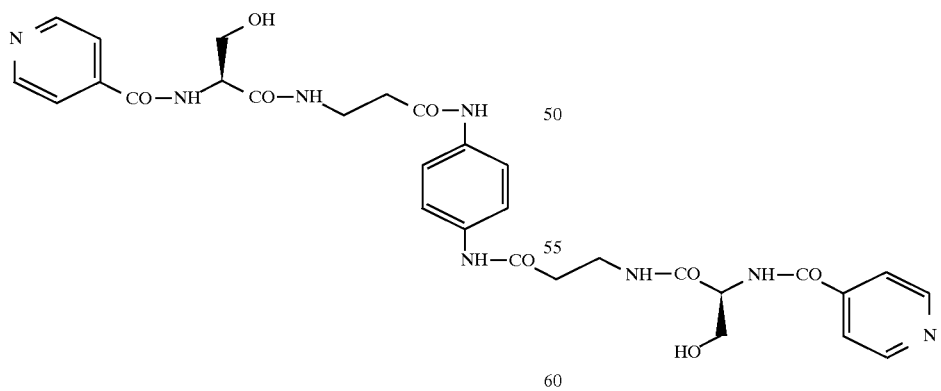

EXAMPLE 7

N,N'-Bis(pyroglutamoyl-glutamoyl-β-alanyl)-1,4-diaminobenzene

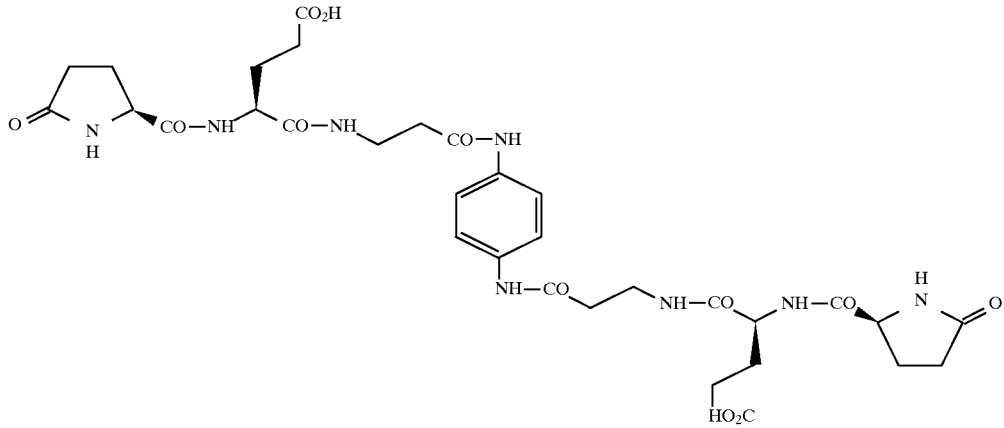

a) N,N'-Bis(BOC-glutamoyl(OBzl)-β-alanyl)-1,4-diaminobenzene

To a solution of N,N'-bis(BOC-β-alanyl)-1,4-diaminobenzene (0.50 g, 1.1 mmol) as prepared in Example 1, in $CH_2Cl_2$ (20 mL) was added TFA (5 mL). The reaction was stirred at room temperature for 2 h. The solvent was removed in vacuo and the residue was dissolved in DMF (5 mL). $EtNiPr_2$ (2.0 mL, 11 mmol), BOC-Glu(OBzl) (1.1 g, 3.3 mmol), HOBt (0.90 g, 6.6 mmol) and BOP reagent (1.5 g, 3.3 mmol) were sequentially added. After 18 h, the reaction was poured into $H_2O$ (100 mL) and $Et_2O$ (50 mL). The resulting precipitate was collected, washed with $Et_2O$ (20 mL), water (50 mL) and dried under vacuum to give a white solid (0.48 g).

MS (ES+) m/z 889.4 (MH$^+$).

b) N,N'-Bis(pyroglutamoyl-glutamoyl(OBzl)-β-alanyl)-1,4-diaminobenzene

To a solution of N,N'-bis(BOC-glutamoyl(OBzl)-β-alanyl)-1,4-diaminobenzene (0.48 g, 0.54 mmol) in $CH_2Cl_2$ (6 mL) was added TFA (3 mL). The reaction was stirred at room temperature for 1 h. The solvent was removed in vacuo and the residue was dissolved in DMF (5 mL). $EtNiPr_2$ (0.94 mL, 5.4 mmol), p-Glu (0.21 g, 1.6 mmol), HOBt (0.44 g, 3.3 mmol) and BOP reagent (0.72 g, 1.6 mmol) were sequentially added. After 48 h, the reaction was poured into a mixture of 1N HCl (50 mL), brine (50 mL) and $Et_2O$ (50 mL). The resulting precipitate was collected and dried under vacuum to give a white solid (0.80 g)

A portion (0.28 g) of the crude material was resuspended in EtOAc (50 mL) and 1N HCl (50 mL). The precipitate was collected, washed with EtOAc (20 mL), water (20 mL) and dried under vacuum to give the desired compound as a white solid (0.11 g).

MS (ES+) m/z 889.4 (MH$^+$).

c) N,N'-Bis(pyroglutamoyl-glutamoyl-β-alanyl)-1,4-diaminobenzene

An HF vessel was charged with N,N'-bis(pyroglutamoyl-glutamoyl(OBzl)-β-alanyl)-1,4-diaminobenzene (30 mg 0.03 mmol). Anhydrous HF (ca. 5 mL) was condensed into the vessel at −78° C. The reaction vessel was sealed and warmed to 0° C. After 1 h, the HF was removed in vacuo, the residue was partitioned between 1% TFA/$H_2O$ (20 mL) and $Et_2O$ (10 mL). The $Et_2O$ layer was discarded and the aqueous phase was lyophilized to give the title compound (27 mg).

$^1$H NMR (400 MHz, DMSO-$d_6$) δ9.88 (s, 2H), 8.11 (d, J=8.0 Hz, 2H), 8.01 (broad s, 2H), 7.79 (s, 2H), 7.49 (s, 4H), 4.23 (m, 2H), 4.06 (m, 2H), 3.30 (m, 4H), 2.50 (m, 8H), 2.30–1.70 (m, 8H).

MS (ES+) m/z 731.2 (MH$^+$); MS (ES−) m/z 729.0 (M-H).

EXAMPLE 8

N-5'-(Pyroglutamoyl-glutamoyl-amino)pentyl-6-(pyroglutamoyl-glutamoyl-amino)hexanamide

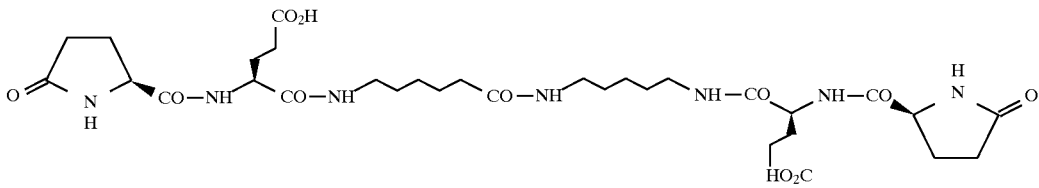

a) N-5'-(BOC-amino)pentyl-6-amino-hexanamide

BOC-ε-Caproic acid (2.10 g, 9.09 mmol), EDC (2.04 g, 10.6 mmol), HOBt (1.44 g, 10.6 mmol) and $EtNiPr_2$ (1.90 mL, 10.9 mmol) were added to a solution of N-BOC-1,5-diaminopentane (1.79 g, 8.86 mmol) in DMF (45 mL). After 24 h at room temperature the reaction was quenched by pouring into water (100 mL) and extracting with EtOAc (3×50 mL). The combined organic extracts were washed with 1N HCl (20 mL), brine (20 mL), dried over $Na_2SO_4$ and concentrated to give a yellow residue. Flash chromatography (10% MeOH/EtOAc, silica gel) gave the desired compound as a white foam (2.97 g, 81%).

b) N-5'-(BOC-glutamoyl(OBzl)-amino)pentyl-6-(BOC-glutamoyl(OBzl)-amino)-hexanamide To a solution of N-5'-(BOC-amino)pentyl-6-amino-hexanamide (0.43 g, 1.04 mmol) in $CH_2Cl_2$ (15 mL) was added TFA (5 mL). The reaction was stirred at room temperature for 1 h. The solvent was removed in vacuo and the residue was dissolved in DMF (5 mL). EtNiPr$_2$ (1.80 mL, 10.3 mmol), BOC-Glu(OBzl) (1.05 g, 3.11 mmol), HOBt (0.84 g, 6.22 mmol) and BOP reagent (1.37 g, 3.10 mmol) were sequentially added. After 18 h, the reaction was poured into a mixture of 1N HCl (50 mL) and brine (50 mL). The aqueous phase was extracted with EtOAc (3×50 mL). The combined organic extracts were washed with 1N HCl (50 mL), brine (50 mL) and dried over Na$_2$SO$_4$. Concentration gave the desired compound (1.93 g).

c) N-5'-(Pyroglutamoyl-glutamoyl(OBzl)-amino)pentyl-6-(pyroglutamoyl-glutamoyl(OBzl)-amino)hexanamide To a solution of N-5'-(BOC-glutamoyl(OBzl)-amino) pentyl-6-(BOC-glutamoyl(OBzl)-amino)hexanamide (1.93 g, 1.04 mmol) in CH$_2$Cl$_2$ (14 mL) was added TFA (6 mL). The reaction was stirred at room temperature for 1 h. The solvent was removed in vacuo and the residue was dissolved in DMF (10 mL). EtNiPr$_2$ (2.70 mL, 15.5 mmol), p-Glu (0.45 g, 3.10 mmol), HOBt (0.42 g, 3.11 mmol) and BOP reagent (1.37 g, 3.10 mmol) were sequentially added. After 48 h, the reaction was poured into a mixture of water (50 mL) and EtOAc. The resulting precipitate was collected, rinsed with Et$_2$O and dried under vacuum to give the desired compound as a white solid.

MS (ES+) m/z 876.2 (MH$^+$); MS (ES−) m/z 920 (m+HCO$_2^-$).

d) N-5'-(Pyroglutamoyl-glutamoyl-amino)pentyl-6-(pyroglutamoyl-glutamoyl-amino)hexanamide An HF vessel was charged with N-5'-(pyroglutamoyl-glutamoyl(OBzl)-amino)pentyl-6-(pyroglutamoyl-glutamoyl(OBzl)-amino)hexanamide (92 mg 0.11 mmol). Anhydrous HF (ca. 5 mL) was condensed into the vessel at −78° C. The reaction vessel was sealed and warmed to 0° C. After 1 h, the HF was removed in vacuo, the residue was partitioned between 1% TFA/H$_2$O (20 mL) and Et$_2$O (10 mL). The Et$_2$O layer was discarded and the aqueous phase was lyophilized to give the title compound (46 mg)

$^1$H NMR (400 MHz, DMSO-d$_6$) δ8.08 (d, J=7.9 Hz, 2H), 7.91 (m, 2H), 7.91 (s, 2H), 7.73 (m, 2H), 4.90 (broad s, 1H), 4.23 (m, 2H), 4.07 (m, 2H), 3.00 (m, 6H), 2.30–2.00 (m, 12H), 1.90 (m, 4H), 1.75 (m, 2H), 1.50–1.38 (m, 8H), 1.24 (m, 4H)

MS (ES+) m/z 696.2 (MH$^+$); MS (ES−) m/z 694.2 (M-H).

EXAMPLE 9

N,N'-Bis(picolinoyl-seryl-β-alanyl)-1,5-diaminonapthalene a) N,N'-Bis(BOC-β-alanyl)-1,5-diaminonapthalene To a suspension of 1,5-diaminonapthalene (0.50 g, 3.16 mmol) in CH$_2$Cl$_2$ (45 mL) was added BOC-β-Ala (1.4 g, 7.4 mmol), EDC (1.3 g, 6.9 mmol), HOBt (0.9 g, 6.7 mmol) and Et$_3$N (1.1 mL, 7.9 mmol). After 2.5 h at reflux, the reaction was allowed to cool to room temperature and quenched by pouring into water (100 mL). The resulting precipitate was collected and dried under vacuum to give the desired compound as a white solid (0.49 g).

MS (ES+) m/z 501.2 (MH$^+$); MS (ES−) m/z 499.0 (M-H).

b) N,N'-Bis(BOC-seryl(Bzl)-β-alanyl)-1,5-diaminonapthalene

To a solution of N,N'-bis(BOC-β-alanyl)-1,5-diaminonapthalene (0.30 g, 0.60 mmol) in CH$_2$Cl$_2$ (9 mL) was added TFA (3 mL). The reaction was stirred at room temperature for 1 h. The solvent was removed in vacuo and the residue was dissolved in DMF (3 mL). EtNiPr$_2$ (1.00 mL, 5.74 mmol), BOC-Ser(Bzl) (0.53 g, 1.80 mmol), HOBt (0.49 g, 3.63 mmol) and BOP reagent (0.80 g, 1.80 mmol) were sequentially added. After 24 h, the reaction was poured into water (100 mL). The resulting precipitate was collected, rinsed with 1N HCl, H$_2$O and dried under vacuum to give the desired compound as a purple solid (0.31 g).

MS (ES+) m/z 855.4 (MH$^+$).

c) N,N'-Bis(picolinoyl-seryl(Bzl)-β-alanyl)-1,5-diaminonapthalene

To a solution of N,N'-bis(BOC-seryl(Bzl)-β-alanyl)-1,5-diaminonapthalene (70 mg, 0.08 mmol) in CH$_2$Cl$_2$ (2 mL) was added TFA (1 mL). The reaction was stirred at room temperature for 1.5 h. The solvent was removed in vacuo and the residue was dissolved in DMF (5 mL). EtNiPr$_2$ (0.14 mL, 0.80 mmol), picolinic acid (0.03 g, 0.24 mmol), HOBt (0.07 g, 0.52 mmol) and BOP reagent (0.11 g, 0.25 mmol) were sequentially added. After 24 h, the reaction was poured into water (50 mL). The resulting precipitate was collected, rinsed with H$_2$O and dried under vacuum to give the desired compound (0.08 g).

MS (ES+) m/z 865.4 (MH$^+$); MS (ES−) m/z 863.2 (M-H).

d) N,N'-Bis(picolinoyl-seryl-β-alanyl)-1,5-diaminonapthalene

An HF vessel was charged with N,N'-bis(picolinoyl-seryl (Bzl)-β-alanyl)-1,5-diaminonapthalene (14 mg 0.02 mmol). Anhydrous HF (ca. 5 mL) was condensed into the vessel at −78° C. The reaction vessel was sealed and warmed to 0° C. After 1 h, the HF was removed in vacuo, the residue was partitioned between 1% TFA/H$_2$O (20 mL) and Et$_2$O (10 mL). The Et$_2$O layer was discarded and the aqueous phase was lyophilized to give the title compound.

$^1$H NMR (400 MHz, DMSO-d$_6$) δ9.95 (s, 2H), 8.70 (m, 4H), 8.25 (m, 2H), 8.05 (m, 4H), 7.90 (m, 2H), 7.65 (m, 4H), 7.50 (m, 2H), 4.50 (m, 2H), 3.70 (m, 4H), 3.35 (m, 4H), 2.70 (m, 4H)

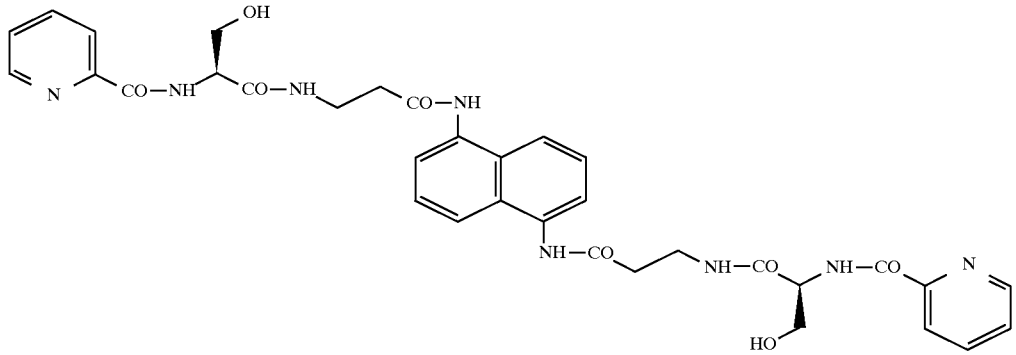

MS (ES+) m/z 685.2 (MH⁺); MS (ES–) m/z 797.2 (M⁻+ TFA).

EXAMPLE 10 trans-N,N'-Bis(picolinoyl-seryl-β-alanyl)-1,4-diaminocyclohexane

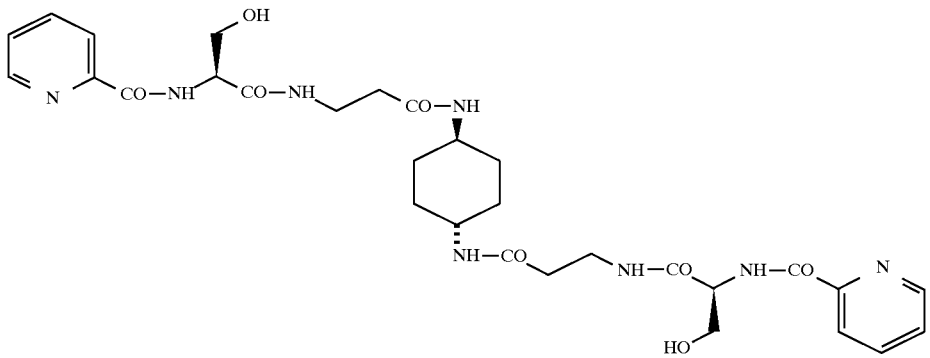

a) trans-N,N'-Bis(BOC-β-alanyl)-1,4-diaminocyclohexane

To a solution of trans-1,4-diaminocyclohexane (0.50 g, 4.38 mmol) in DMF (25 mL) was added BOC-β-Ala (2.48 g, 13.1 mmol), HOBt (3.55 g, 26.3 mmol), BOP reagent (5.81 g, 13.1 mmol) and EtNiPr₂ (7.60 mL, 43.6 mmol). After 20 h at room temperature, the reaction was poured into a mixture of ice, 1N HCl (150 mL) and Et₂O (50 mL). The resulting precipitate was collected, washed with 1N HCl, EtOAc and dried under vacuum to give the desired compound as a white powder (1.80 g).

MS (ES+) m/z 457.2 (MH⁺).

b) trans-N,N'-Bis(BOC-seryl(Bzl)-β-alanyl)-1,4-diaminocyclohexane

To a solution of trans-N,N'-bis(BOC-β-alanyl)-1,4-diaminocyclohexane (1.00 g, 2.19 mmol) in CH₂Cl₂ (30 mL) was added TFA (10 mL). The reaction was stirred at room temperature for 1 h. The solvent was removed in vacuo and the residue was dissolved in DMF (10 mL). EtNiPr₂ (3.80 mL, 21.8 mmol), BOC-Ser(Bzl) (1.94 g, 6.57 mmol), HOBt (1.78 g, 13.2 mmol) and BOP reagent (2.91 g, 6.58 mmol) were sequentially added. After 2.5 h, the reaction was poured into a mixture of ice, 1N HCl (100 mL) and Et₂O (50 mL). The resulting precipitate was collected, rinsed with H₂O and dried under vacuum to give the desired compound (1.44 g).

MS (ES+) m/z 811.4 (MH⁺).

c) trans-N,N'-Bis(picolinoyl-seryl(Bzl)-β-alanyl)-1,4-diaminocyclohexane

To a solution of trans-N,N'-bis(BOC-seryl(Bzl)-β-alanyl)-1,4-diaminocyclohexane (1.09 g, 1.35 mmol) in CH₂Cl₂ (18 mL) was added TFA (6 mL). The reaction was stirred at room temperature for 1 h. The solvent was removed in vacuo and the residue was dissolved in DMF (6 mL). EtNiPr₂ (2.35 mL, 13.5 mmol), picolinic acid (0.50 g, 4.06 mmol), HOBt (1.09 g, 8.07 mmol) and BOP reagent (1.79 g, 4.05 mmol) were sequentially added. After 6 h, the reaction was poured into a mixture of brine (100 mL) and Et₂O (50 mL). The resulting precipitate was collected, rinsed with H₂O and dried under vacuum to give the desired compound (1.04 g).

MS (ES+) m/z 821.4 (MH⁺).

d) trans-N,N'-Bis(picolinoyl-seryl-β-alanyl)-1,4-diaminocyclohexane

An HF vessel was charged with trans-N,N'-Bis(picolinoyl-seryl(Bzl)-β-alanyl)-1,4-diaminocyclohexane (26 mg 0.03 mmol). Anhydrous HF (ca. 5 mL) was condensed into the vessel at –78° C. The reaction vessel was sealed and warmed to 0° C. After 1 h, the HF was removed in vacuo, the residue was partitioned between 1% TFA/H₂O (20 mL) and Et₂O (10 mL). The Et₂O layer was discarded and the aqueous phase was lyophilized to give the title compound.

¹H NMR (400 MHz, DMSO-d₆) δ8.66 (m, 4H), 8.36 (m, 2H), 8.05 (m, 6H), 7.60 (m, 2H), 5.41 (m, 1H), 5.08 (m, 1H), 4.41 (m, 1H), 3.70 (m, 5H), 3.45 (m, 2H), 3.27 (m, 4H), 2.21 (m, 4H), 1.74 (m, 4H), 1.17 (m, 4H)

MS (ES+) m/z 641.2 (MH⁺).

EXAMPLE 11

N,N'-Bis(3,4-dehydroprolyl-seryl-β-alanyl)-1,4-diaminobenzene

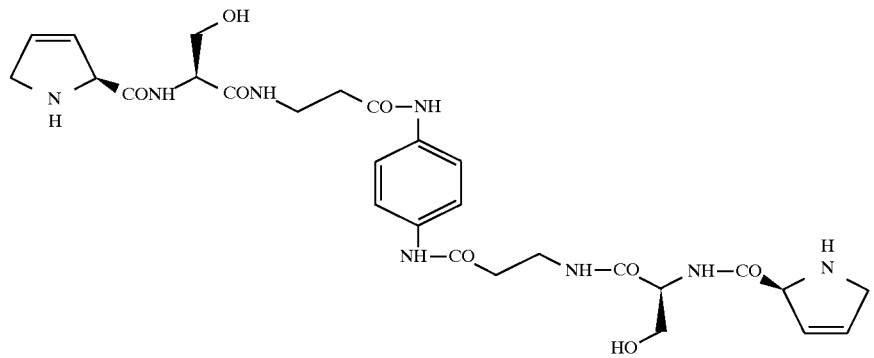

a) N,N'-Bis(3,4-dehydroprolyl-seryl(Bzl)-β-alanyl)-1,4-diaminobenzene

In a manner similar to Example 1(c), N,N'-bis(BOC-seryl (Bzl)-β-alanyl)-1,4-diaminobenzene (0.38 g, 0.35 mmol) was reacted with TFA (10 mL) in CH$_2$Cl$_2$ (10 mL). After 1 h, the solvent was removed in vacuo and the residue dissolved in DMP (2 mL). A portion of this solution (1 mL)was removed and reacted in a manner similar to Example 1(c) with EtNiPr$_2$ (0.10 mL, 0.57 mmol), BOC-3,4-dehydroproline (0.11 g, 0.53 mmol), HOBt (0.12 g, 0.86 mmol) and BOP reagent (0.24 g, 0.53 mmol) to give a white precipitate. Flash chromatography (10% MeOH/EtOAc, silica gel) gave pure product (73 mg).

MS (ES+) m/z 995.4 (MH$^+$).

b) N,N'-Bis(3,4-dehydroprolyl-seryl-β-alanyl)-1,4-diaminobenzene

In a manner similar to Example 1(d), N,N'-bis(3,4-dehydroprolyl-seryl(Bzl)-β-alanyl)-1,4-diarninobenzene (41.1 mg, 0.041 μmol) was reacted with anhydrous HF (ca. 5 mL) to give crude product (28.1 mg). Preparative reverse phase HPLC (5% to 80% CH$_3$CN/H$_2$O and 0.1% TFA, Hamilton PRP-1 column) gave 15.1 mg (59%) of the title compound as a white solid.

MS (ES+) m/z 615.2 (MH$^+$).

EXAMPLE 12

N,N'-Bis(2-pyrrole carbonyl-seryl-β-alanyl)-1,4-diaminobenzene a) N,N'-Bis(2-pyrrole carbonyl-seryl(Nzl)-β-alanyl)-1,4-diaminobenzene N,N'Bis(BOC-seryl(Bzl)-β-alanyl)-1,4-diaminobenzene (387 mg, 3601 μmol) prepared as in Example 1 was suspended in CH$_2$Cl$_2$ (15 mL) and neat TFA (15 mL) was added, causing the mixture to become homogeneous immediately. After stirring for 90 min at room temperature, the mixture was concentrated in vacuo to an oil, which was taken up in DMF (1 mL) and neutralized with DIEA (400 μL, 2.3 mmol).

Pyrrole-2-carboxylic acid (69 mg, 624 μmol) was dissolved in SOCl$_2$ (2.5 mL) and stirred at −20° C. for 1 h. The solvent was removed in vacuo to give a white solid which was dissolved in CH$_2$Cl$_2$ (1 mL). The deprotected compound obtained above was taken up in CH$_2$Cl$_2$ (2 mL) with a few drops of DMF and neutralized with DIEA (650 μL, 3.73 mmol). Half of this solution (1 mL, ca. 180 μmol) was added to the acid chloride solution at −20° C. Additional DIEA (100 μL, 574 μmol) was added and the reaction was stirred for 18 h, while warming gradually to room temperature. The reaction was added to a rapidly-stirred mixture of Et$_2$O (50 mL) and 5% Na$_2$CO$_3$ in brine (100 mL), resulting in formation of a white precipitate. The solid was removed by filtration and stored under high vacuum to dry. Purification by flash chromatography (20% MeOH/EtOAc, silica gel) afforded 18 mg (12%) of the desired compound.

MS (ES+) m/z 791.4 (MH$^+$).

b) N,N'-Bis(2-pyrrole carbonyl-seryl-β-alanyl)-1,4-diaminobenzene

N,N'-Bis(2-pyrrole carbonyl-seryl(Nzl)-β-alanyl)-1,4-diarninobenzene (14 mg, 17 μmol) was dissolved in p-cresol (0.5 mL) in a 50-mL Teflon HF cleavage vessel fitted with a magnetic stirring bar. The vessel was cooled to −78° C. and evacuated using a water aspirator. Anhydrous HF (ca. 5 mL) was condensed into the vessel, the cooling bath was changed to 0° C., and the reaction was stirred for 1 h. The HF was carefully removed under aspirator vacuum, the residue was taken up in Et$_2$O (25 mL), then extracted with H$_2$O (4×25 mL) and 0.1N HOAc (1×25 mL). The combined aqueous

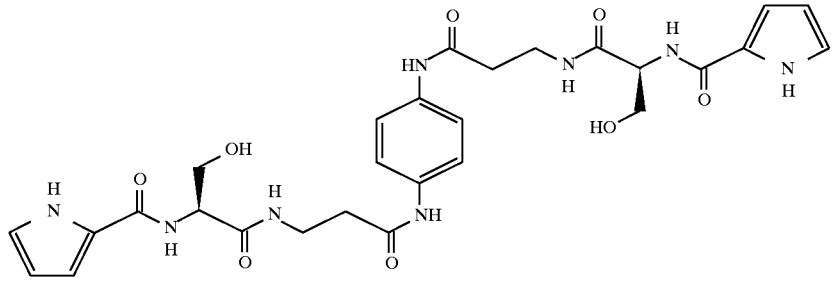

layers were concentrated in vacuo to less than one-third volume, frozen and lyophilized to a white powder. Purification by reverse-phase HPLC (CH$_3$CN/H$_2$O+0.1% TFA, gradient, Hamilton PRP-1) gave 7 mg (66%) of the title compound.

MS (ES+) m/z 611.2 (MH$^+$).

EXAMPLE 13

N,N'-Bis(prolyl-seryl-β-alanyl)-1,4-diaminobenzene

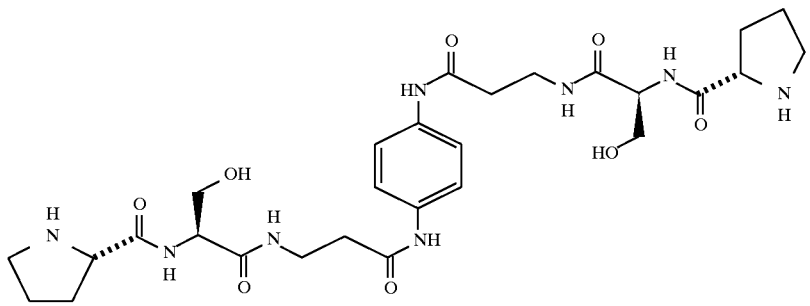

a) N,N'-Bis(BOC-prolyl-seryl(Bzl)-β-alanyl)-1,4-diaminobenzene

N,N'-Bis(BOC-seryl(Bzl)-β-alanyl)-1,4-diaminobenzene (101 mg, 126 μmol) prepared as in Example 1, was suspended in CH₂Cl₂ (2 mL) and neat TFA (2 mL) was added, causing the mixture to become homogeneous immediately. After stirring for 90 min at room temperature, the mixture was concentrated in vacuo to an oil, which was taken up in DMF (1 mL) and neutralized with DIEA (400 μL, 2.3 mmol). The solution was added to a vial containing HOBt (84 mg, 623 μmol) and Boc-Pro (137 mg, 636 μmol). BOP reagent (284 mg, 643 μmol) was added and the reaction was stirred for 18 h. The reaction was then added to a rapidly stirred mixture of Et₂O (50 mL), 1N HCl (50 mL), and brine (50 mL), resulting in formation of a white precipitate. After stirring for 20 min, the precipitate was removed by filtration and dried in a vacuum dessicator. Flash chromatography (10% MeOH/EtOAc, silica gel) gave 78 mg (62%) of the title compound as a white powder.

MS (ESI) m/z 999.4 (MH⁺).

b) N,N'-Bis(prolyl-seryl-β-alanyl)-1,4-diaminobenzene

In an analogous fashion to Example 12(b), N,N'-bis(BOC-prolyl-seryl(Bzl)-β-alanyl)-1,4-diaminobenzene (32 mg, 32 μmol), anisole (0.5 mL, used in place of p-cresol) and HF (5 mL) gave 13 mg (65%) of the title compound after reverse phase HPLC purification (CH₃CN/H₂O+0.1% TFA gradient, Hamilton PRP-1 column).

MS (ES+) m/z 619.4 (MH⁺).

EXAMPLE 14

N,N'-Bis (azetidine carbonyl-seryl-β-alanyl)-1,4-diaminobenzene

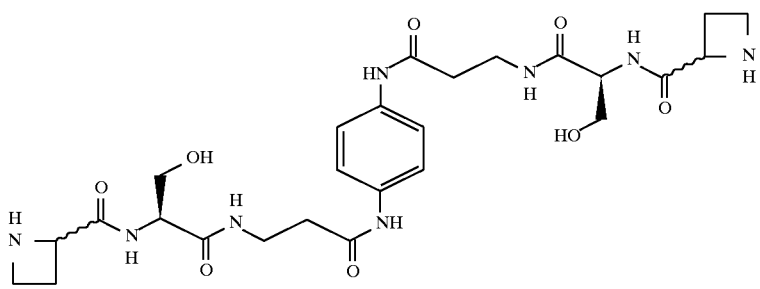

a) N-BOC-azetidine carboxylic acid

To a suspension of azetidine-2-carboxylic acid (1.04 g, 10.3 mmol) in dioxane (25 mL) was added 5% NaHCO₃ (25 mL) and n-butanol (3 mL). Di-t-butyl dicarbonate (2.23 g, 10.2 mmol) was added and the reaction was stirred for 24 h at room temperature. The reaction was quenched by adding H₂O (50 mL) and CHCl₃ (100 mL). The mixture was acidified to pH2 by the careful addition of 3N H₂SO₄. After separating the phases, the aqueous layer was extracted further with CHCl₃ (2×50 mL). The combined organic layers were washed with 1N HCl (2×50 mL), dried over Na₂SO₄, filtered, and concentrated in vacuo to a clear oil. Recrystallization from EtOAc/hexane yielded 1.56 g of the desired compound. The mother liquor was concentrated n vacuo to give another 406 mg of the desired product (95%).

MS (ES+) m/z 202.0 (MH⁺).

b) N,N'-Bis(BOC-azetidine carbonyl-seryl-β-alanyl)-1,4-diaminobenzene

In an analogous fashion to Example 13(a), deprotection of N,N'-bis(BOC-seryl(Bzl)-β-alanyl)-1,4-diaminobenzene (102 mg, 126 μmol) in CH₂Cl₂ (1 mL) and TFA (1 mL) followed by reaction with DIEA (220 μL, 1.3 mmol), HOBt (86 mg, 637 μmol), N-BOC-azetidine carboxylic acid (76 mg, 378 μmol), and BOP reagent (281 mg, 636 μmol) in DMF (1 mL) gave 43 mg (36%) of the desired compound as a white powder after flash chromatography (15% MeOH/EtOAc, silica gel).

MS (ES+) m/z 971.4 (MH⁺).

c) N,N'-Bis(azetidine carbonyl-seryl-β-alanyl)-1,4-diaminobenzene

In an analogous fashion to Example 12(b), N,N'-bis(BOC-azetidine carbonyl-seryl(Bzl)-β-alanyl)-1,4-diaminobenzene (31 mg, 32 μmol), anisole (0.5 mL, used in place of p-cresol) and HF (5 mL) gave 14 mg (75%) of the title compound as two diastereomers (from the azetidine carboxylic acid, isolated seperately without assigning the absolute stereochemistry) after reverse phase HPLC purification (CH₃CN/H₂O+0.1% TFA gradient, Hamilton PRP-1 column).

MS (ES+) m/z 591.2 (MH⁺).

EXAMPLE 15

N,N'-Bis (picolinoyl-N-methyl-seryl-β-alanyl)-1,4-diaminobenzene

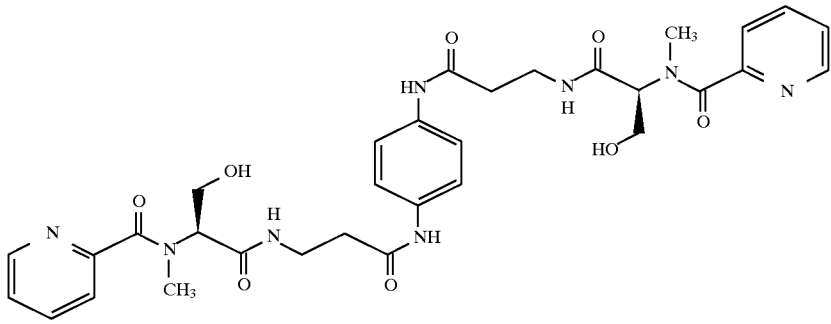

a) N,N'-Bis(Fmoc-N-methyl-seryl-β-alanyl)-1,4-diaminobenzene

N,N'Bis(BOC-β-alanyl)-1,4-diaminobenzene (90 mg, 199 μmol) prepared as in Example 1 was suspended in CH$_2$Cl$_2$ (1 mL) and neat TFA (1 mL) was added, causing the mixture to become homogeneous immediately. After stirring for 90 min at room temperature, the mixture was concentrated in vacuo to an orange oil, which was taken up in DMF (1 mL) and neutralized with DIEA (420 μL, 2.4 mmol).

Fmoc-N-MeSer(Bzl) (259 mg, 601 μmol) was dissolved in DMF (5 mL). HOBt (135 mg, 997 μmol) and BOP reagent (267 mg, 604 μmol) were added and the mixture was stirred for 5 min. The activated amino acid was then added to the product obtained above and the reaction was stirred for 18 h. The reaction was added to a rapidly-stirred mixture of Et$_2$O (50 mL) and 5% Na$_2$CO$_3$ in brine (100 mL), resulting in formation of a white precipitate. This was collected and dried under vacuum to obtain 259 mg of the desired product as a white powder. This was used in the next step without further purification.

MS (ES+) m/z 1077.4 (MH$^+$).

b) N,N'-Bis(picolinoyl-N-methyl-seryl(Bzl)-β-alanyl)-1,4-diaminobenzene

N,N'-Bis(Fmoc-N-methyl-seryl-β-alanyl)-1,4-diaminobenzene (129 mg, 120 μmol) was dissolved in CH$_2$Cl$_2$ (1.6 mL). Piperidine (400 μL) was added and the reaction was stirred for 90 min. The reaction mixture was concentrated in vacuo to a tan solid after azeotroping several times with toluene. The compound was stored under high vacuum for ca. 5 h to remove traces of piperidine. After separation of the phases, the aqueous layer was extracted with CHCl$_3$ (2×50 mL) and the combined organic layers were washed with H$_2$O (2×50 mL) and brine (1×50 mL). Drying the organic layer over Na$_2$SO$_4$, followed by filtration and solvent removal in vacuo, gave a yellow oil which was purified by flash chromatography (5% MeOH/EtOAc, silica gel) to afford 77 mg (76%) of the desired compound.

MS (ES+) m/z 843.4 (MH$^+$).

c) N,N'-Bis(picolinoyl-N-methyl-seryl-β-alanyl)-1,4-diaminobenzene

In an analogous fashion to Example 12(b), N,N'-bis(picolinoyl-N-methyl-seryl(Bzl)-β-alanyl)-1,4-diaminobenzene (69 mg, 82 μmol), p-cresol (0.5 mL) and HF (5 mL) gave 23 mg (41%) of the title compound after reverse phase HPLC purification (CH$_3$CN/H$_2$O+0.1% TFA gradient, Hamilton PRP-1 column).

MS (ES+) m/z 663.2 (MH$^+$).

EXAMPLE 16

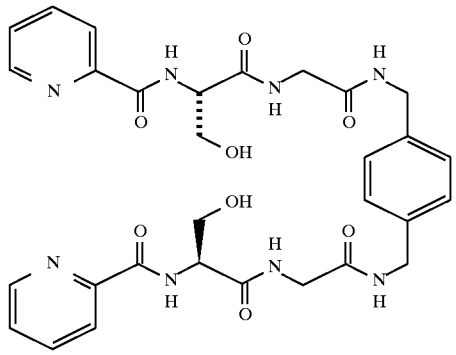

Preparation of (Pic-Ser-Gly)$_2$-α,α'-diamino-p-xylene a) (Boc-Gly)$_2$-PDAX: Boc-Gly-OH (876 mg, 5 mmol) was dissolved in CH$_2$Cl$_2$ (25 mL), HOBt (676 mg, 5 mmol) and DCC (1032 mg, 5 mmol) were added and the mixture was stirred for 15 min. Precipitated DCU was filtered off and washed with CH$_2$Cl$_2$ (5 mL). The combined filtrate and washing were added to a prepared solution of α,α'-diamino-p-xylene (PDAX; 341 mg, 2.5 mmol) and Pr$^i{}_2$NEt (0.92 mL, 5 mmol) in CH$_2$Cl$_2$ (25 mL). A precipitate was formed immediately. The mixture was stirred overnight and was then rotary evaporated and dried under high vacuum. The residue was triturated with 5% aq NaHCO$_3$ (50 mL) and the product extracted into CH$_2$Cl$_2$ (total 150 mL; some MeOH was added to aid dissolution). The combined extracts were dried on MgSO$_4$, filtered and evaporated to dryness. The residue was reprecipitated from Et$_2$O and filtered. After drying, the title compound (958 mg, 85.1%) was obtained as a very white soft powder. TLC R$_f$0.44 (85:10:5 CHCl$_3$/MeOH/AcOH).

b) (Z-Ser(t-Bu)-Gly)$_2$-PDAX: (Boc-Gly)$_2$-PDAX (400 mg, 0.89 mmol) was dissolved in 1% H$_2$OCF$_3$COOH (40 mL) and the solution stirred for 90 min. It was then rotary evaporated, coevaporated twice with PhMe (10 mL each) and dried under high vacuum. The oily residue of (H-Gly)$_2$-PDAX.2CF$_3$COOH was redissolved in DMF (15 mL) and added to Z-Ser(t-Bu)-OH (680 mg, 1.77 mmol), preactivated with PyBOP (923 mg, 1.77 mmol), HOBt (240 mg, 1.77 mmol) and NMM (0.49 mL, 4.43 mmol) in DMF (5 mL). The mixture was stirred overnight, evaporated under water-pump vacuum at 60°, treated with 5% aq NaHCO$_3$ (50 mL) and extracted into CH$_2$Cl$_2$ (3×25 mL). The combined extracts were washed with 10% aq citric acid and 2M aq NaCl (25 mL each), dried on MgSO$_4$, filtered, evaporated and taken to dryness under high vacuum. The title compound was obtained as a colorless oil. TLC R$_f$0.57 (85:10:5 CHCl$_3$/MeOH/AcOH).

c) (Pic-Ser(t-Bu)-Gly)$_2$-PDAX: (Z-Ser(t-Bu)-Gly)$_2$-PDAX (ca. 0.89 mmol) was dissolved in MeOH (50 mL) and hydrogenolysed for 90 min over 10% Pd/C catalyst (300 mg) as usual. The catalyst was removed by filtration through Celite filter aid. The filtrate was rotary evaporated and further dried under high vacuum. The intermediate (H-Ser (t-Bu)-Gly)$_2$-PDAX was redissolved in DMF (15 mL) and reacted with Pic-OH (219 mg, 1.78 mmol), preactivated with PyBOP (926 mg, 1.78 mmol), HOBt (240 mg, 1.78 mmol) and NMM (0.29 mL, 2.67 mmol) in DMF (5 mL). The mixture was stirred overnight, evaporated, treated with 5% aq NaHCO$_3$ (50 mL) and extracted into CH$_2$Cl$_2$ (3×25 mL). The combined extracts were washed with 2M aq NaCl (25 mL), dried over MgSO$_4$, filtered and evaporated. The residue was purified by flash chromatography (3 cm column, 7.5% MeOH/CH$_2$Cl$_2$ eluant). The title compound was obtained as a slightly discolored oil. TLC R$_f$0.45 (85:10:5 CHCl$_3$/MeOH/AcOH).

d) (Pic-Ser-Gly)$_2$-PDAX: (Pic-Ser(t-Bu)-Gly)$_2$-PDAX (ca. 0.89 mmol) was dissolved in 1% H$_2$O/CF$_3$COOH (40 mL) and the solution stirred for 90 min. It was then rotary evaporated to a small volume and the peptide precipitated by the addition of Et$_2$O (50 mL). The peptide was collected by centrifugation (3 min, 2,500 r.p.m.) and decantation of the ethreal supernatant. The pellet was washed once more with Et$_2$O in a similar fashion. After drying (first under N$_2$ stream and then under high vacuum), the title compound was obtained as a slightly discolored powder (386 mg, 68.3% over 4 steps). An aliquot of this material (32.5 mg) was suspended in 0.1% aq CF$_3$COOH (4.5 mL) and neat CF$_3$COOH (0.25 mL) was added to solubilise the sample. This was filtered and chromatographed on a Supelco C$_{18}$HPLC column (2.5×25 cm; 10 mm particles) by elution with a gradient of 6 to 24% NeCN in 0.1% aq CF$_3$COOH over 1 h at 10mL/min. Fractions which were pure by analytical HPLC (Vydac 218TP54, 1 mL/min, 9 to 30% MeCN in 0.1% aq CF$_3$COOH over 20 min; tR 14.8 min) were pooled and lyophilised to provide the pure peptide (23 mg, 71% purification yield). FAB-MS: C$_{30}$H$_{34}$N$_8$O$_8$= 634.65; observe [M+H]$^+$635.2, [M+NA]$^+$657.2.

EXAMPLES 17 and 18

(Apy-L-Ser-βAla)$_2$-terephthalate and (Apy-D-Ser-βAla)$_2$-terephthalate

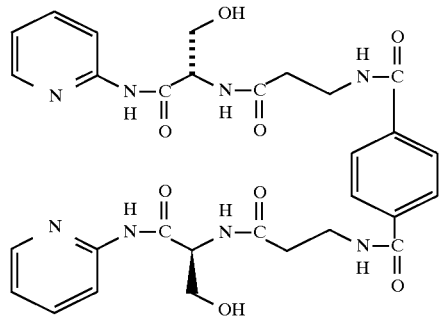

-continued

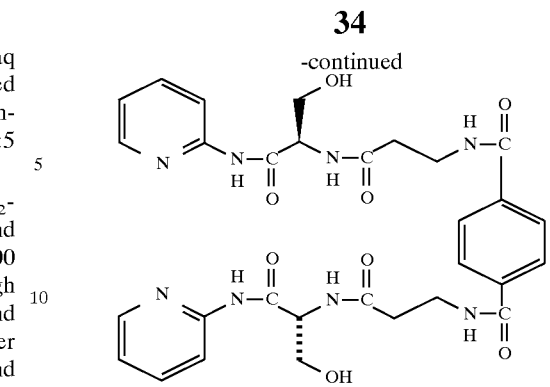

(The synthesis of the above compounds were carried out in parallel) Preparation of (Apy-L-Ser-βAla)$_2$-terephthalate and (Apy-D-Ser-βAla)$_2$-terephthalate a) Z-Ser(t-Bu)-Apy: Z-L-Ser(t-Bu)-OH or Z-D-Ser(t-Bu) -OH (1.92 g, 5 mmol) was dissolved in CH$_2$Cl$_2$ (25 mL). HOBt (0.68 g, 5 mmol) and DCC (1.03 g, 5 mmol) were added. The mixture was stirred for 15 min, then the DCU was filtered off. The filtrate was added to a solution of 2-aminopyridine (Apy; 0.47 g, 5 mmol) and i-Pr$_2$NEt (0.87 mL, 5 mmol) in CH$_2$Cl$_2$ (25 mL) and the entire mixture was stirred overnight. It was then diluted to 100 mL with additional CH$_2$Cl$_2$ and extracted with 5% aq NaHCO$_3$ (2×25 mL) and 2M aq NaCl (25 mL). The organic phase was dried over MgSO$_4$, filtered and evaporated. The residue was purified by flash chromatography (3 cm diam. column; 7.5% Et$_2$O/CH$_2$Cl$_2$) to yield 444 mg (23.9%) or 373 mg (26.1%) of glassy solid L- or D-product, respectively. TLC R$_f$0.70 (85:10:5 CHCl$_3$/MeOH/AcOH).

b) Z-βAla-(L and D) Ser(t-Bu)-Apy; Z-Ser(t-Bu)-Apy (444 mg, 1.2 mmol) was dissolved in MeOH (50 mL) and hydrogenated using 10% Pd/C (120 mg). After a reaction period of 1 h, the catalyst was filtered off and the filtrate evaporated to dryness. The intermediate H-Ser(t-Bu)-Apy (TLC:R$_f$0.15; 85:10:5 CHCl$_3$/MeOH/AcOH; UV & ninhydrin) was redissolved in DMF (25 mL) and added to a prepared solution of Z-βAla-OH (268 mg, 1.2 mmol), PyBOP (624 mg, 1.2 mmol), HOBt (162 mg, 1.2 mmol) and NMM (0.26 mL, 1.8 mmol) in DMF (5 mL). The mixture was stirred overnight, evaporated, triturated with 5% aq NaHCO$_3$ (50 mL) and extracted into CH$_2$Cl$_2$ (3×30 mL). The extract was washed with 2M aq NaCl (25 mL), dried over MgSO$_4$, filtered and evaporated. The title compound was obtained as a colourless oil (TLC R$_f$0.56, 85:10:5 CHCl$_3$/MeOH/AcOH).

c) (Apy-(L and D) Ser(t-Bu)βAla)$_2$-terephthalate: Z-βAla-Ser(t-Bu)-Apy (ca. 1.2 mmol) was hydrogenated as described above and the intermediate H-βAla-Ser(t-Bu)-Apy was redissolved in DMF (25 mL) and reacted with a prepared solution of terephthalic acid (100 mg, 0.6 mmol), PyBOP (624 mg, 1.2 mmol), HOBt (162 mg, 1.2 mmol) and NMM (0.26 mmol, 1.8 mmol) in DMF (5 mL) overnight. After evaporation to dryness, the residue was triturated with 5% aq NaHCO$_3$ (50 mL) and was extracted into CH$_2$Cl$_2$ (3×30 mL). The extract was washed with 2M aq NaCl (25 mL), dried over MgSO$_4$, filtered and evaporated. The residue was purified by flash chromatography (3 cm diam, column; eluant 7.5% MeOH/CH$_2$Cl$_2$). The title compound (c) was obtained as a slightly discoloured oil. TLC R$_f$0.53 (85:10:5 CHCl$_3$/MeOH/AcOH).

d) (Apy-L-Ser-βAla)$_2$-terephthalate and (Apy-D-Ser-βAla)$_2$-tere-phthlate: The product from the previous step was dissolved in 1% H$_2$O/CF$_3$COOH (40 mL) and the mixture stirred for 90 min. It was then evaporated to a small volume and the peptide precipitated by the addition of Et$_2$O (50 mL). It was collected by centrifugation (3 min, 2,500 r.p.m.) and decantation of the supernatant. The pellet was washed once more with Et$_2$O in a similar fashion. After drying, the peptide was obtained in a yield of 222 mg (58% w.r.t. Z-L-Ser(t-Bu)-Apy) or 217 mg (57% w.r.t Z-D-Ser(t-Bu)-Apy), respectively. An aliquot of this material (30.9 mg or 34.2 mg of L- and D-isomers, respectively) was chromatographed on a Vydac 218TP1022 HPLC column at 9 mL/min with a gradient from 3 to 15% MeCN in 0.1% CF$_3$COOH/H$_2$O over 60 min. Fractions which were pure by analytical HPLC (Vydac 218TP54, 1 mL/min, 3 to 12% MeCN in 0.1% aq CF$_3$COOH over 20 min; $t_R$1.70 min) were pooled and lyophilised to provide the pure peptide (24.6 mg or 26.0 mg, 79.6% or 76.0% purification yields for the L- and D-isomers, respectively). FAB-MS: C$_{30}$H$_{34}$N$_8$O$_8$= 634.65; observe [M+H]$^+$635.2. (l-isomer), [M+H]$^+$635.3 (D-isomer. $[\alpha]_D^{20}$=−32.8 or +32.4±0.5 (c=0.5; 0.1% CF$_3$COOH/H$_2$O) for L- and D-isomer, respectively.

EXAMPLE 19

Formulations for pharmaceutical use incorporating compounds of the present invention can be prepared in various forms and with numerous excipients. Examples of such formulations are given below.

| Tablets/Ingredients | Per Tablet |
|---|---|
| 1. Active ingredient (Cpd of Form. I or II) | 0.5 mg |
| 2. Corn Starch | 20 mg |
| 3. Alginic acid | 20 mg |
| 4. Sodium alginate | 20 mg |
| 5. Mg stearate | 1.3 mg |

Procedure for tablets:
Step 1 Blend ingredients No. 1, No. 2, No. 3 and No. 4 in a suitable mixer/blender.
Step 2 Add sufficient water portion-wise to the blend from Step 1 with careful mixing after each addition. Such additions of water and mixing until the mass is of a consistency to permit its converion to wet granules.
Step 3 The wet mass is converted to granules by passing it through an oscillating granulator using a No. 8 mesh (2.38 mm) screen.
Step 4 The wet granules are then dried in an oven at 140° F. (60° C.) until dry.
Step 5 The dry granules are lubricated with ingredient No. 5.
Step 6 The lubricated granules are compressed on a suitable tablet press.

Parenteral Formulation

A pharmaceutical composition for parenteral administration is prepared by dissolving an appropriate amount of a compound of formula I or II in polyethylene glycol with heating. This solution is then diluted with water for injections Ph Eur. (to 100 ml). The solution is then sterilized by filtration through a 0.22 micron membrane filter and sealed in sterile containers.

We claim:

1. A compound of Formula (I):

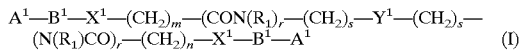

wherein:
A$^1$ is independently proline, dehydroproline, pyroglutamic acid, glutamine, tyrosine, glutamic acid, picolinic acid, oxothiazolidine carboxylic acid, pipecolinic acid, piperidine carboxylic acid, pyrrole carboxylic acid, isopyrrole carboxylic acid, pyrazole carboxylic acid, isoimidazole carboxylic acid, triazole carboxylic acid, isoxazole carboxylic acid, oxazole carboxylic acid, thiazole carboxylic acid, isothiazole carboxylic acid, oxadiazole carboxylic acid, oxatriazole carboxylic acid, oxazine carboxylic acid, oxathiazole carboxylic acid, dioxazole carboxylic acid, pyrimidine carboxylic acid, pyridazine carboxylic acid, pyrazine carboxylic acid, piperazine carboxylic acid, triazine carboxylic acid, isooxazine carboxylic acid, oxathiazene carboxylic acid, morpholine carboxylic acid, indole carboxylic acid, indolenene carboxylic acid, 2-isobenzazole carboxylic acid, 1,5-pyridine carboxylic acid, pyranol-pyrrole carboxylic acid, isoindazole carboxylic acid, indoxazine carboxylic acid, benzoxazole carboxylic acid, cinnoline carboxylic acid, quinazolene carboxylic acid, pyrido-pyridine carboxylic acid, pyrido-pyridine carboxylic acid, pyrido-pyridine carboxylic acid, 1,3,2-benzoxazine carboxylic acid, 1,4,2-benzoxazine carboxylic acid, 2,3,1-benzoxazine carboxylic acid, 3,1,4-benzoxazine carboxylic acid, 1,2-benzisoxazine carboxylic acid, 1,4-benzisoxazine carboxylic acid, carbazole carboxylic acid, acridine carboxylic acid, purine carboxylic acid, hydroxypicolinic acid, hydantoin carboxylic acid, N-acetyl proline, or azetidine carboxylic acid;

B$^1$ is independently serine, glutamic acid, tyrosine, aspartic acid, hydroxyproline, O-benzyl serine, N-methyl serine, N-methyl threonine, N-methyl glutamic acid, N-methyl tyrosine, N-methyl aspartic acid, 2-amino-3-hydroxythiopropanoic acid, 2-amino-1-hydroxypropyl or 2-amino-1-hydroxypent-3-enyl;

X$^1$ is O, S, NR$_1$ or CR$_2$R$_3$;

Y$^1$ is O, S, NR$_1$, CR$_2$R$_3$, imidazolyl, triazolyl, oxazolyl, pyridyl, pyrimidyl, pyrazolyl, pyrrolyl, furanyl, thienyl, phenyl, benzyl, phenethyl, naphthyl, C$_{2-5}$ alkyl, C$_{2-5}$ alkenyl, or C$_{2-5}$ alkynyl, napthyl, xylyl, CON(R$_3$), piperazine, biphenyl, diacetylene benzene or divinyl benzene;

R$_1$, R$_2$ and R$_3$ are independently hydrogen, C$_{1-4}$ alkyl, C$_{2-4}$ alkenyl or C$_{2-4}$ alkynyl, C$_{3-7}$ cycloalkyl, imidazolyl triazolyl, oxazolyl, pyridyl, pyrimidyl, pyrazolyl, pyrrolyl, furanyl, thienyl, phenyl, benzyl, phenethyl, naphthyl all of which may be substituted by one or more C$_{1-3}$ alkyl groups;

m and n are independently 0 to 5;

r is 0 to 2; and s is 0 or 1;

or a pharmaceutically acceptable salt thereof.

2. A compound according to claim 1 wherein A$^1$ is pyroglutamic acid, picolinic acid, proline, pipecolenic acid, dehydroproline, azetidine carboxylic acid or pyrole carboxylic acid; B$^1$ is glutamic acid, serine, aspartic acid or N-methyl serine; X$^1$ is NR$_1$; m and n are 1 or 2 and Y$^1$ is phenyl or xylyl; r is 1 and s is 0.

3. A compound of formula II:

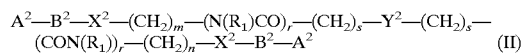

wherein:
A$^2$ is independently 3-aminopyrazole, 5-aminopyrazole, aminothiazole, aminopyrimidine, aminothiadiazole, aminopyridazine, 2-aminopyridine, 3-aminopyridine, 4-aminopyridine, aminopurine, aminopteridine, 3-aminoisoxazole, 5-aminoisoxazole, 3-amino-1,2,4-triazine, 2-amino-1,3,5-triazine, aminodimethyluracil, aminomethyluracil, 2-amino-3-hydroxypyridine, 2-amino-4-hydroxpyridine, 3-(aminomethyl)pyridine, 4-(aminomethyl)pyridine, aniline, 3-aminopyrrolidine, aminoquinoline, aminotetrazole, 3-amino-1,2,4-triazole, 5-aminouracil, 6-aminouracil, aminopyrrole, aminofuran, aminothiophene, 3-aminopiperidine, 4-aminopiperidine, cyclohexylamine, cyclopentylamine, pyrazolo pyridine, 3-aminobutyrolactam or 2-aminocyclopentinone, $B^2$ is independently serine, threonine, glutamic acid, tyrosine, aspartic acid, hydroxyproline, O-benzyl serine, N-methyl serine, N-methyl threonine, N-methyl glutamic acid, N-methyl tyrosine, or N-methyl aspartic acid, $X^2$ is CO or $CR_2R_3$;

$Y^2$ is O, S, $NR_1$, $CR_2R_3$, imidazolyl, triazolyl, oxazolyl, pyridyl, pyrimidyl, pyrazolyl, pyrrolyl, furanyl, thienyl, phenyl, benzyl, phenethyl, naphthyl, $C_{2-5}$ alkyl, $C_{2-5}$ alkenyl, $C_{2-5}$ alkynyl, napthyl, xylyl, $CON(R_3)$, piperazine, biphenyl, diacetylene, benzene or divinyl benzene;

$R_1$, $R_2$ and $R_3$ are independently hydrogen, $C_{1-4}$ alkyl, $C_{2-4}$ alkenyl or $C_{2-4}$ alkynyl, $C_{3-7}$ cycloalkyl, imidazolyl triazolyl, oxazolyl, pyridyl, pyrimidyl, pyrazolyl, pyrrolyl, furanyl, thienyl, phenyl, benzyl, phenethyl, naphthyl, all of which may be substituted by one or more $C_{1-3}$ alkyl groups;

m and n are independently 0 to 5;

r is 0 to 2; and s is 0 or 1;

or a pharmaceutically acceptable salt thereof.

4. A compound according to claim 3 wherein $A^2$ is 2-aminopyridine or, 3-aminopyrrolidine; $B^2$ is serine; $X^2$ is CO; m and n are 2, s is 0, Y is phenyl and r is 1.

5. A compound according to claim 1 selected from:

N,N'-Bis(picolinyl-seryl-β-alanyl)-1,4-diaminobenzene;

N,N'-Bis(pyroglutamyl-glutamyl-β-alanyl)-1,4-diaminobenzene; and

N,N'-Bis(dehydroprolyl-seryl-β-alanyl)-1,4-diaminobenzene

N,N'-Bis(picolinoyl-seryl-glycol)-1,4-diaminoxylene

N,N'-Bis(prolyl-seryl-β-alaryl)-1,4-diaminobenzene

N,N'-Bis(azetidinyl-seryl-β-alaryl)-1,4-diaminobenzene

N,N'-Bis(picolinoyl-N-methylseryl-β-alaryl)-1,4-diaminobenzene

N,N'-Bis(pyrrolyl-seryl-β-alaryl)-1,4-diaminobenzene.

6. A pharmaceutical composition comprising a compound of claim 1 and a pharmaceutically acceptable carrier.

7. A method of stimulating the myelopoietic system which comprises administering to a subject in need thereof, an effect amount of a compound according to claim 1.

8. A method of treating viral, fungal and bacterial infections which comprises administering to a subject in need thereof, an effective amount of a compound of claim 1.

9. A method of treating Candida or Herpes infections which comprises administering to a subject in need thereof, an effective amount of a compound of claim 1.

10. A pharmaceutical composition comprising a compound of claim 3 and a pharmaceutically acceptable carrier.

11. A method of stimulating the myelopoietic system which comprises administering to a subject in need thereof, an effect amount of a compound according to claim 3.

12. A method of treating viral, fungal and bacterial infections which comprises administering to a subject in need thereof, an effective amount of a compound of claim 3.

13. A method of treating Candida or Herpes infections which comprises administering to a subject in need thereof, an effective amount of a compound of claim 3.

* * * * *